(12) United States Patent
Ingber et al.

(10) Patent No.: US 10,293,023 B2
(45) Date of Patent: May 21, 2019

(54) METHOD OF ALTERING VASCULAR PERMEABILITY AND USES THEREOF

(71) Applicant: CHILDREN'S MEDICAL CENTER CORPORATION, Boston, MA (US)

(72) Inventors: Donald E. Ingber, Boston, MA (US); Akiko Mammoto, Brookline, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 212 days.

(21) Appl. No.: 14/771,359

(22) PCT Filed: Mar. 14, 2014

(86) PCT No.: PCT/US2014/026975
§ 371 (c)(1),
(2) Date: Aug. 28, 2015

(87) PCT Pub. No.: WO2014/152122
PCT Pub. Date: Sep. 25, 2014

(65) Prior Publication Data
US 2016/0008421 A1 Jan. 14, 2016

Related U.S. Application Data

(60) Provisional application No. 61/788,714, filed on Mar. 15, 2013.

(51) Int. Cl.
| | | |
|---|---|---|
| *C12N 15/11* | (2006.01) | |
| *A61K 31/08* | (2006.01) | |
| *A61K 38/10* | (2006.01) | |
| *A61K 31/275* | (2006.01) | |
| *A61K 31/713* | (2006.01) | |
| *A61K 38/18* | (2006.01) | |
| *A61K 38/39* | (2006.01) | |
| *A61K 38/44* | (2006.01) | |
| *C07K 16/28* | (2006.01) | |
| *C12N 15/113* | (2010.01) | |
| *A61K 31/519* | (2006.01) | |
| *A61N 5/06* | (2006.01) | |
| *C07K 16/40* | (2006.01) | |
| *A61K 39/00* | (2006.01) | |
| *A61K 48/00* | (2006.01) | |

(52) U.S. Cl.
CPC ............ *A61K 38/10* (2013.01); *A61K 31/275* (2013.01); *A61K 31/519* (2013.01); *A61K 31/713* (2013.01); *A61K 38/1841* (2013.01); *A61K 38/39* (2013.01); *A61K 38/44* (2013.01); *A61N 5/062* (2013.01); *C07K 16/28* (2013.01); *C07K 16/40* (2013.01); *C12N 15/1137* (2013.01); *A61K 48/005* (2013.01); *A61K 2039/505* (2013.01); *A61N 2005/0661* (2013.01); *C07K 2317/33* (2013.01); *C07K 2317/34* (2013.01); *C07K 2317/76* (2013.01); *C12N 2310/14* (2013.01); *C12Y 104/03013* (2013.01)

(58) Field of Classification Search
CPC .. A01K 2207/05; C12N 15/113; A61K 38/10; A61K 48/005; A61K 2039/505
See application file for complete search history.

(56) References Cited

U.S. PATENT DOCUMENTS

| | | |
|---|---|---|
| 8,283,350 B2 | 10/2012 | Horn |
| 8,377,987 B2 | 2/2013 | Lau et al. |
| 8,383,787 B2 | 2/2013 | Yedgar |
| 2007/0021365 A1 | 1/2007 | Erler et al. |
| 2009/0104201 A1* | 4/2009 | Smith ............... C07K 16/40 424/139.1 |
| 2009/0216177 A1 | 8/2009 | Akiyama et al. |
| 2009/0226447 A1 | 9/2009 | Boone et al. |
| 2010/0317721 A1* | 12/2010 | Neufeld ............ C12N 15/1137 514/44 R |
| 2012/0129757 A1* | 5/2012 | Li ..................... A61K 38/1709 514/1.1 |
| 2015/0086565 A1* | 3/2015 | Hynes ............. G01N 33/57419 424/158.1 |

FOREIGN PATENT DOCUMENTS

| | | |
|---|---|---|
| CA | 2548739 C | 8/2009 |
| WO | 2001/45751 A1 | 6/2001 |

OTHER PUBLICATIONS

Written Opinion of the International Searching Authority for international application PCT/US14/26975, dated Nov. 5, 2014, pp. 1-5 (dated 2014).*
Taylor et al. Neoplasia 13 2011, 406-418 (Year: 2011).*
(Continued)

*Primary Examiner* — Brian Whiteman
(74) *Attorney, Agent, or Firm* — Nixon Peabody LLP; David S. Resnick; Nicole D. Kling

(57) ABSTRACT

Provided here are methods of modulating vascular permeability by changing the mechanical properties of extracellular matrices (ECM) and methods of treatment of diseases, conditions and symptoms related to vascular permeability such as pulmonary edema and acute respiratory distress syndrome (ARDS). The modulation can be increasing or decreasing vascular permeability. Vascular leakage can be normalized by increasing or decreasing ECM stiffness depending on the baseline mechanical properties of the tissue or organ. Vascular permeability is altered by changing the mechanical properties of ECM by administering a lysyl oxidase modulating (LOX) agent.

3 Claims, 7 Drawing Sheets
Specification includes a Sequence Listing.

(56) References Cited

OTHER PUBLICATIONS

Li et al. Respiration 2012: 84:509-517 (Year: 2012).*
Rodriguez et al. Drug News Perspect 21. 2008, 218-224 (Year: 2008).*
Chetta et al, "Role of inhaled steroids in vascular airway remodelling in asthma and COPD", Int J Endocrinology, 2012: 1-6 (2012).
Kuetemeyer et al, "Two-photon induced collagen cross-taking in bioartificial cardiac tissue", Opt Express, 19(17): 15996-16007 (2011).
Mammoto et al., "Angiopoietin-1 Requires p190 RhoGAP to Protect against Vascular Leakage in Vivo", The J of Biological Chemistry, 282(33): 23910-23918 (2007).
Mendes et al., "Airway Blood Flow Reactivity in Healthy Smokers and in Ex-Smokers With or Without COPD", Chest, 129(4): 893-898 (2006).
Mimic-Oca et al., "Free radicals in cardiovascular diseases", Facts Universitatis, 6(1): 11-22 (1999).
Ohkubo et al., "Interleukin 2 Induced Leukocyte Adhesion to the Normal and Tumor Microvascular Endothelium in Vivo and Its Inhibition by Dextran Sulfate: Implications for Vascular Leak Syndrome", Cancer Res, 51: 1561-1563 (1991).
Perina, "Noncardiogenic pulmonary edema", Emerg Med Clin North Am, 21: 385-393 (2003).

* cited by examiner

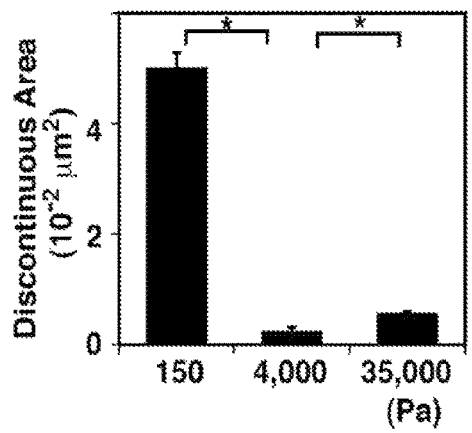
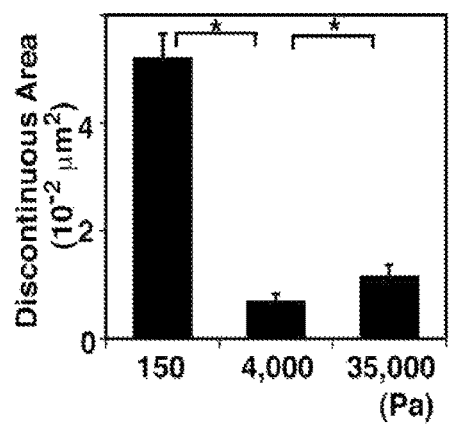
FIGs. 6A-6B
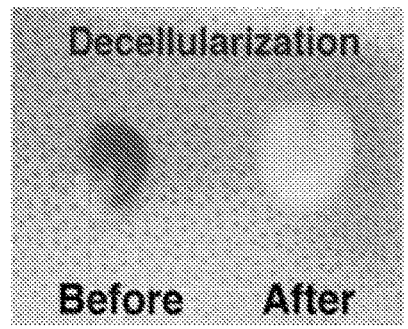
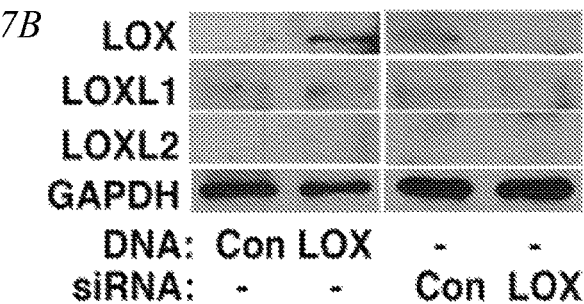
FIGs. 7A-7B

SEQUENCE LISTING

<160> NUMBER OF SEQ ID NOS: 7

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Glu Asp Thr Ser Cys Asp Tyr Gly Tyr His Arg Arg Phe Ala
1               5                   10

<210> SEQ ID NO 2
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2
caacgggcag guguucag                                                     18

<210> SEQ ID NO 3
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3
cugaacaccu gcccguug                                                     18

```
<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagacgccac tgtcgcttt                                                 19

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtctttgga actttgtctg caa                                            23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcttctgctg cgtgacaacc                                                20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagaaaccag cttggaacca g                                              21
```

METHOD OF ALTERING VASCULAR PERMEABILITY AND USES THEREOF

CROSS-REFERENCE TO RELATED APPLICATIONS

This application is a 35 U.S.C. § 371 National Phase Entry Application of International Application No. PCT/US2014/026975 filed Mar. 14, 2014, which designates the U.S., and which claims benefit under 35 U.S.C. § 119(e) of U.S. Provisional Application No. 61/788,714 filed Mar. 15, 2013, the contents of which are incorporated herein by reference in their entirety.

GOVERNMENT SUPPORT

This invention was made with government support under grant number CA045548, awarded by the National Institutes of Health, and grant number W81XWH-05-1-0115, awarded by the U.S. Department of the Army The Government has certain rights in the invention.

SEQUENCE LISTING

The instant application contains a Sequence Listing which has been submitted electronically in ASCII format and is hereby incorporated by reference in its entirety. Said ASCII copy, created on Jul. 29, 2014, is named 701039- 077091-PCT_SL.txt and is 1,947 bytes in size.

BACKGROUND

Vascular permeability is tightly regulated during blood vessel development and it is indispensable for normal organ function throughout adult life. Many life-threatening pathological conditions, including acute respiratory distress syndrome (ARDS), atherosclerosis, cancer, and organ failure are caused or complicated by compromised vascular barrier function. In ARDS—a devastating pulmonary complication that often occurs with sepsis caused by systemic infection—excess fluid leaks out of the lung capillaries and fills the adjacent alveolar air spaces causing pulmonary edema; this fluid impairs gas exchange across the alveolar membrane, decreases lung compliance and severely compromises respiratory function. ARDS occurs in almost half of severe sepsis cases in human patients and combination of sepsis and ARDS is associated with a mortality of 60%. Despite a great amount of effort in this area, currently there is no specific clinical therapy for ARDS or any other condition caused by abnormal vascular permeability. Accordingly, there is a need in the art for modulating vascular permeability and treatments for conditions wherein vascular permeability plays a part.

SUMMARY OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The following embodiments and aspects thereof are described and illustrated in conjunction with compositions and methods which are meant to be exemplary and illustrative, not limiting in scope.

Embodiments of the present invention are based on the discovery that physical changes in extracellular matrix (ECM) actively regulate cell-to-cell junction integrity and consequently regulate vascular permeability.

The inventors show herein that vascular permeability is controlled mechanically by changes in the ECM structure. For example, the inventors showed that vascular leakage can be increased by altering ECM compliance and by manipulating LOX-mediated collagen cross-linking using the enzyme lysyl oxidase (LOX). Either decreasing or increasing ECM stiffness relative to normal levels disrupts junctional integrity and increases vascular leakage. It is known that aberrant vascular permeability occur to many diseases and conditions. For example, endotoxin-induced increases of vascular permeability are accompanied by associated increases in ECM rigidity and LOX activity.

Accordingly, this discovery provides a strategy to manipulate vascular permeability as clinically desired by inducing or introducing physical changes in the ECM. The manipulation of vascular permeability can be to decrease permeability when there is an undesirable increase in permeability such as during an infection or in acute respiratory distress syndrome (ARDS). Vascular leakage can be normalized by increasing or decreasing ECM stiffness depending on the baseline mechanical properties of the tissue or organ. Alternatively, the manipulation of vascular permeability can be to increase permeability when an induced increase in permeability is beneficial and served to deliver therapeutics to target sites in a subject undergoing a treatment. For example, vascular permeability is altered by changing the mechanical properties of ECM by administering a lysyl oxidase modulating (LOX) agent.

Accordingly, it is the objective of the present disclosure to provide novel methods for manipulating or changing the vascular permeability in a tissue or organ by changing the mechanical properties of the ECM.

It is also the objective of the present disclosure to provide methods of treating diseases and conditions that have aberrant, abnormal or undesired level of vascular permeability by changing the mechanical properties of the ECM. Non-limiting examples of such diseases and conditions include pulmonary edema and acute respiratory distress syndrome (ARDS).

It is also the objective of the present disclosure to provide methods of treating diseases and conditions that can benefit from an increased level of vascular permeability by changing the mechanical properties of the ECM. The increase in permeability served to deliver therapeutics to target sites. Non-limiting examples of such diseases and conditions include cancers.

Accordingly, provided herein are methods for altering vascular permeability in a tissue or organ, methods of treating vascular permeability, and methods for increasing ECM cross linking.

In one embodiment, provide herein is a method of altering vascular permeability in a tissue or organ, comprising administering an agent that modulates the mechanical properties of the extracellular matrix (ECM) to a subject in need thereof. For example, when it is clinically desirable to increase the vascular permeability in a tissue or organ in a subject; or when it is clinically desirable to decrease the vascular permeability in a tissue or organ in a subject.

In another embodiment, provide herein is a method of altering vascular permeability in a tissue or organ, comprising providing a biopsy sample of the tissue or organ, analyzing the mechanical properties of the ECM in the tissue or organ sample, comparing with a normal range, and when the mechanical properties are increase or decrease from the normal range by at least 10%, then administering an agent that modulates the mechanical properties of the extracellular matrix (ECM) to a subject in need thereof in order to normalize the vascular leakage.

In another embodiment, provide herein is a method of treating a pulmonary disease in a subject in need thereof comprising administering to the lung an agent that modulates the mechanical properties of the extracellular matrix (ECM) of the lungs.

In another embodiment, provide herein is a method of treating a disease or condition in a subject in need thereof where edema is a symptom of the disease or condition, comprising administering to the subject an agent that modulates the mechanical properties of the extracellular matrix (ECM) in the subject.

In another embodiment, provide herein is a method of treating a disease or condition in a subject in need thereof where edema is a symptom of the disease or condition, the method comprising providing a biopsy sample of a tissue or organ that is affected by the disease or condition, measuring the mechanical properties of the ECM in the tissue or organ sample, comparing with a normal range of measured mechanical properties of the ECM in the tissue or organ, and when the mechanical properties are increase or decrease from the normal range by at least 10%, administering an agent that modulates the mechanical properties of the extracellular matrix (ECM) to a subject in need thereof in order to normalize the vascular leakage.

In another embodiment, provide herein is a method of treating cancer in a subject in need thereof comprising administering to the subject an agent that modulates the mechanical properties of the extracellular matrix (ECM) in the subject, where the modulation increases the vascular permeability of the cancer affected tissue in the subject.

In various embodiments of the methods described herein, the agent modulates the mechanical properties of the ECM by altering ECM production, ECM deposition, ECM crosslinking, ECM alignment, ECM degradation, ECM composition, ECM surface topography, ECM prestress, or combinations thereof.

As used herein, the term "modulate" when used in the context of an agent and in reference to ECM mechanical properties means an increase or a decrease of the ECM mechanical properties disclosed herein and also those known to one skilled in the art. Assessing and measuring ECM mechanical properties can be performed by any method known to the skilled artisan.

The term "agent" refers to any entity which is normally not present or not present at the levels being administered to a cell, tissue, organ or subject. Agent can be selected from a group comprising: chemicals; small molecules; nucleic acid sequences; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

In some embodiments, the ECM mechanical properties include but are not limited to stiffness, elastic recoil, and viscoelasticity.

In various embodiments of the methods described herein, the method can further comprise measuring the ECM, tissue, or organ mechanics in the subject before treatment. In various embodiments, measuring ECM mechanics can comprise measuring stiffness, elastic recoil, viscoelasticity, or combinations thereof. In various embodiments, measuring ECM, tissue, or organ mechanics can be by clinical, optical imaging, histopathological or physical methods. In various embodiments, the clinical, optical imaging, histopathological or physical methods can comprise atomic force microscopy, magnetic cytometry, rheometry, characterization of tissue stress-strain relationships, or combinations thereof.

In various embodiments of the methods described herein, when the tissue or organ has stiffness above a normal range for the tissue or organ, for example, more than at least 10% of a normal range, the method then comprises administering an agent that decreases the stiffness of the ECM. The aim is to normalize the ECM stiffness, and thereby normalize the vascular leakage. As used herein, the term "normalize" in the context of ECM stiffness, ECM mechanical properties and vascular leakage means bringing the respective parameter closer to the normal value or range for that parameter in a typical healthy, non-cancer, non-disease, non-infected situation.

In one embodiment of the methods described herein, the normal range for vascular permeability for a particular tissue or organ is the vascular permeability for the same particular tissue or organ from a healthy subject. For example, if the tissue is the lung, then the normal range of vascular permeability is obtained from the healthy lungs of a healthy subject. In other embodiments, the normal range is the vascular permeability for the same particular tissue or organ from the same subject, except the vascular permeability is from a non-disease portion of the tissue or organ. For example, if the tissue is the kidney, only one kidney is diseased with cancer, then the normal range of vascular permeability is obtained from the other healthy kidney of the same subject. In other embodiments, the normal range is the average vascular permeability for the same tissue or organ from a population of healthy subjects. In other embodiments, the normal range is the average plus one or two standard deviations of vascular permeability for the same tissue or organ from a population of healthy subjects. In some embodiments, the population of healthy subjects can range from at least three healthy individuals to 25 healthy individuals, and even more than 50 healthy individuals.

Similarly, in some embodiment of the methods described herein, the normal range for ECM stiffness or ECM mechanical properties for a particular tissue or organ is the respective parameter for the same particular tissue or organ from a healthy subject, or from a non-disease portion of the tissue or organ from the same subject, or same particular tissue or organ from a population of healthy subjects. In other embodiments, the normal range is the average ECM stiffness or respective ECM mechanical properties for the same tissue or organ from a population of healthy subjects. In other embodiments, the normal range is the average plus one or two standard deviations of ECM stiffness or respective ECM mechanical properties for the same tissue or organ from a population of healthy subjects. In some embodiments, the population of healthy subjects can range from at least three healthy individuals to 25 healthy individuals, and even more than 50 healthy individuals.

In various embodiments of the methods described herein, the subject is a mammal. In other embodiments, the subject is a primate mammal, such as a monkey, a baboon, a chimpanzee. In other embodiments, the subject is a human.

In various embodiments of the methods described herein, the agent decreases ECM production, deposition, cross-linking, alignment, prestress, or combinations thereof, or the agent increases ECM degradation, thereby decreasing tissue or organ stiffness.

In various embodiments of the methods described herein, the agent is an expression vector encoding a nucleic acid or the agent is a synthetic modified RNA, and the encoded a nucleic acid or synthetic modified RNA decreases ECM production, ECM deposition, ECM cross-linking, ECM alignment, ECM prestress, or combinations thereof, or increases ECM degradation, thereby decreasing tissue or organ stiffness.

In various embodiments of the methods described herein, the agent decreases ECM deposition. In some embodiments, the ECM deposited comprises proteoglycans such as heparan sulfate, chondroitin sulfate, keratan sulfate; non-proteoglycan polysaccharide such as hyaluronic acid; fibers such as collagen, elastin; and other components such as fibronectin and laminin.

In various embodiments of the methods described herein, the agent is a proline analogue, a retinoid, an inhibitor of prolyl hydroxylase, an inhibitor of collagen cross-linking, an active collagen modulator, an angiostatic steroid or heparin. In certain embodiments, the proline analogue can be 1-azetidine-2-carboxylic acid, cis-hydroxyproline,d,L-3,4-dehydroproline, or thioproline. In particular embodiments, the inhibitor of prolyl hydroxylase can be alpha, alpha-dipyridyl. In various embodiments, the inhibitor of collagen cross-linking can be beta-aminopropionitrile (BAPN).

In various embodiments of the methods described herein, the agent is an expression vector encoding a nucleic acid or the agent is a nucleic acid.

The term "nucleic acid" or "nucleic acid sequence" refers to deoxyribonucleotides or ribonucleotides and polymers thereof ("polynucleotides") in either single- or double-stranded form, such as genomic DNA, cDNA, mRNA, ssRNA, dsRNA, etc. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). Nucleotides are indicated by their bases by the following standard abbreviations: adenine (A), cytosine (C), thymine (T), and guanine (G). The nucleic acid molecule can be naturally occurring, as in genomic DNA, or it may be synthetic, ie., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In various embodiments of the methods described herein, the nucleic acid decreases the expression of a gene. For example, a microRNA, dsRNA, LNA, ssRNA, and siRNA, all of which have the ultimate effect of decreasing the expression of a gene.

In various embodiments of the methods described herein, the nucleic acid increases the expression of a gene. For example, a microRNA or a gene coding nucleic acid that have the ultimate effect of increasing the expression of a gene.

In various embodiments of the methods described herein, the agent decreases lysyl oxidase (LOX) activity or expression. In various embodiments, the agent is a LOX inhibitor. In various embodiments of the methods described herein, the agent is an expression vector encoding a LOX inhibitor. In this embodiment, the expression vector encoding a LOX inhibitor is a nucleic acid inhibitor or a protein inhibitor or a peptide inhibitor. The protein or peptide inhibitor inhibits the LOX activity.

In various embodiments of the methods described herein, the LOX inhibitor is a nucleic acid inhibitor that decreases the expression of a LOX gene. In various embodiments, the nucleic acid inhibitor is a nucleic acid sequence that is complementary to a LOX gene and decreases the expression of the LOX gene. In various embodiments, the nucleic acid inhibitor is a single stranded RNA (ssRNA). In various embodiments, the nucleic acid inhibitor is a doubles-stranded RNA (dsRNA). In various embodiments, the nucleic acid inhibitor is a small interference RNA (siRNA). In various embodiments, the nucleic acid inhibitor comprises locked nucleic acid (LNA). In various embodiments, the nucleic acid inhibitor comprises at least 50% LNA. In various embodiments, the nucleic acid inhibitor is a microRNA that has the ultimate effect of decreasing or inhibiting a LOX gene expression. For example, the microRNA regulates the transcription factors involved with the expression of the LOX gene.

The term "gene" or "coding sequence" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

In various embodiments of the methods described herein, the LOX inhibitor is a small molecule inhibitor of the LOX enzyme activity. In various embodiments, the LOX inhibitor is BAPN.

In various embodiments of the methods described herein, the LOX inhibitor is a protein inhibitor or peptide inhibitor of the LOX enzyme activity.

In various embodiments of the methods described herein, the LOX inhibitor is a LOX siRNA In various embodiments of the methods described herein, the LOX inhibitor is a molecule that inhibits LOX enzyme activity. For example, the collagen cross-linking activity.

In various embodiments of the methods described herein, the LOX inhibitor can be the peptide that inhibits LOX activity.

In various embodiments of the methods described herein, the LOX inhibitor is a peptide having at least 90% sequence identity with the sequence EDTSCDYGYHRRFA (SEQ ID NO: 1). In various embodiments of the methods described herein, the LOX inhibitor is a peptide having a percent homology of at least 90% with an amino acid sequence of the sequence EDTSCDYGYHRRFA (SEQ ID NO: 1). In certain embodiments, the peptide has the sequence EDTSCDYGYHRRFA (SEQ ID NO: 1), or be a fragment thereof.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods in the art.

As used herein, "percent homology" in the context of amino acid sequence includes percent identity and percent similarity Amino acid sequence are similar if they do not have the same amino acids, ie. identical amino acids, but have conservative amino acid substitution of the relevant amino acids.

As used herein, the term "conservative amino acid substitution" is one in which the amino acid residue is replaced with an amino acid residue having a side chain with a similar charge and size. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In various embodiments of the methods described herein, the LOX inhibitor is an antibody, or a fragment thereof. In certain embodiments, the antibody is a purified antibody that binds specifically to a 10-20 amino acid polypeptide of a LOX protein. In certain embodiments, the antibody is a purified antibody that binds specifically to a 6-12 amino acid polypeptide of a LOX protein, and inhibits LOX activity. In certain embodiments, the antibody is a purified antibody that binds specifically to the sequence EDTSCDYGYHRRFA (SEQ ID NO: 1) or a sequence having at least 80% identity, and inhibits LOX activity.

In various embodiments of the methods described herein, the LOX activity-inhibiting antibody is covalently bonded to a co-polymer. For example, poly[N-(2-hydroxypropyl)-methacrylamide] (HPMA); diblock-copolymers such as poly(ethylene glycol) (PEG) and poly(ε-caprolactone) (PCL); or amphiphilic triblock copolymer, Pluronic, consisting of poly(ethylene oxide) (PEO) and poly(propylene oxide) (PPO) blocks with a PEO-PPO-PEO structure. In certain embodiments, the co-polymer can be poly(D,L-lactide-co-glycolide)-block-poly(ethylene glycol). Co-polymers and method of conjugating antibodies to the co-polymers are known in the art.

In various embodiments of the methods described herein, the LOX activity inhibiting antibody is covalently bonded to a nanoparticle. For example, nanoparticles of CdTe/ZnS core/shell quantum dots (QDs) were encapsulated in carboxylated Pluronic F127 triblock polymeric micelle; gold nanoparticles, single-wall carbon nanotubes, liposomes, quantum dots, niosomes, dendrimers, polymeric micelles, and polymeric nanoparticles.

In various embodiments of the methods described herein, the LOX inhibitor is an expression vector encoding a nucleic acid that inhibits the expression of a LOX gene.

As used herein, in one embodiment, the term "inhibit" or "inhibition" or "decrease" when used in the context of gene expression means the reduction or prevention of expression of the gene; ie., reduction or prevention of successful transcription and/or translation of gene into protein. In some embodiments, inhibition includes slowing the rate of transcription and/or translation of gene into protein. The reduction or prevention of expression can be by about 20%, about 30%, about 40%, about 50%, about 60%, about 70%, about 80%, about 90%, about 100%, about 125%, about 150% or more compared to in the absence of the inhibitor.

In another embodiment, the term "inhibit" or "inhibition" or "decrease" when used in the context of the LOX activity means the reduction or prevention of the LOX enzymatic activity, specifically catalysis of the cross-linking of the collagen and elastin fibres. The reduction or prevention of LOX activity can be by about 20%, about 30%, about 40%, about 50%, about 60%, about 70%, about 80%, about 90%, about 100%, about 125%, about 150% or more compared to in the absence of the inhibitor.

In various embodiments of the methods described herein, when the tissue or organ has a stiffness below a normal range for the tissue or organ, the method comprise administering an agent that increases the rigidity or stiffness of the ECM.

In various embodiments of the methods described herein, the agent, or an expression vector or synthetic modified RNA encoding such agents, increases ECM production, deposition, cross-linking, alignment, prestress, or combinations thereof, or decreases ECM degradation, thereby increasing tissue or organ stiffness.

In various embodiments of the methods described herein, the agent is an expression vector encoding a nucleic acid or the agent is a synthetic modified RNA, and the encoded a nucleic acid or synthetic modified RNA increases ECM production, ECM deposition, ECM cross-linking, ECM alignment, ECM prestress, or combinations thereof, or increases ECM degradation, thereby increasing tissue or organ stiffness.

In various embodiments of the methods described herein, the agent increases ECM deposition. In some embodiments, the ECM deposited comprises proteoglycans such as heparan sulfate, chondroitin sulfate, keratan sulfate; non-proteoglycan polysaccharide such as hyaluronic acid; fibers such as collagen, elastin; and other components such as fibronectin and laminin.

In various embodiments of the methods described herein, the agent increases LOX activity or expression.

In various embodiments of the methods described herein, the agent is an expression vector encoding a LOX.

As used herein, the term "expression vector" refers to a vector that has the ability to incorporate and express heterologous nucleic acid fragments in a cell. An expression vector can comprise additional elements, for example, the expression vector can have two replication systems, thus allowing it to be maintained in two organisms, for example in human cells for expression and in a prokaryotic host for cloning and amplification.

In various embodiments of the methods described herein, the agent can be a fibronectin-derived peptide. For example, a peptide fragment of fibronectin, or peptide fragment of fibronectin that is modified or conjugated to another molecule.

In various embodiments of the methods described herein, the agent is a LOX enzyme or an enzyme that increases ECM cross-linking.

As used herein, the term "increase" when used in the context of ECM production, ECM deposition, ECM cross-linking, ECM alignment, ECM prestress, ECM degradation, tissue or organ stiffness, or LOX activity or expression means that the increase in the respective parameter is at least 5%, at least 10%, at least 20%, at least 30%, at least 50%, at least 100%, at least 200%, at least 300%, at least 500%, at least 1000%, or more and including all the percentages between 10-1000% over in comparison to the normal range for the respective parameter or over in comparison to the respective parameter prior to administering the agent concerned.

In various embodiments of the methods described herein, the agent is an agent that glycosylates an ECM protein or an agent capable of post-translational modification of the ECM protein.

In various embodiments of the methods described herein, the agent is a microRNA capable of increasing LOX expression.

In various embodiments of the methods described herein, the agent can be a TGF-beta family member.

In various embodiments of the methods described herein, the agent increases production of an ECM molecule.

In various embodiments of the methods described herein, the agent that modulates the mechanical properties of the ECM is administered via an aerosol route, an intravenous route, a parenteral route or a transdermal route. In certain embodiments, the agent is administered via aerosol delivery into the subject's lung.

In various embodiments of the methods described herein, the altering vascular permeability can treat certain diseases and conditions.

As used herein, the term "altering" when used in the context of vascular permeability means either to increase or decrease the vascular permeability prior to treatment or administering the agent described.

In various embodiments of the methods described herein, altering vascular permeability can treat a pulmonary disease or condition selected from the group consisting of pulmonary edema, acute respiratory distress syndrome (ARDS), endotoxin-induced lung injury, pulmonary fibrosis, pulmonary embolism, pulmonary vascular hypertension, emphysema, pleural effusion, lung inflammation, sepsis, and combinations thereof.

In various embodiments of the methods described herein, altering vascular permeability can treat inflammation, or an inflammatory disease or condition selected from the group consisting of arthritis, Crohn's disease, inflammatory bowel disease, Alzheimer's disease, diabetes, gout, atherosclerosis, vasculitis, infection, sepsis, and combinations thereof.

In various embodiments of the methods described herein, altering vascular permeability can treat a primary or metastatic cancer selected from the group consisting of breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

In various embodiments of the methods described herein, altering vascular permeability can enhance delivery and/or effectiveness of a drug. In certain embodiments, the drug can be an anti-cancer drug.

In various embodiments of the methods described herein, altering vascular permeability can treat an aberrant response to a chemical therapy. In particular embodiments, the chemical therapy is IL-2 or interferon-alpha therapy.

In various embodiments of the methods described herein, altering vascular permeability can be used to treat a disease or condition cause by an airborne toxicant. In particular embodiments, the disease or condition cause by an airborne toxicant is caused by smoke or other particulate inhalation or molecular or chemical inhalation.

In various embodiments of the methods described herein, altering vascular permeability treats a disease or condition cause by an infectious agent. In various embodiments of the methods described herein, the disease or condition cause by an infectious agent is caused by a virus, bacteria, fungus, parasite or toxin. For example, excessive pulmonary edema caused by infection by pathogens or toxins from these pathogens: *Streptococcus pneumonia, Staphylococcus aureus, Bacillus anthracia, Haemophilus influenzae, Klebsiella pneumoniae, Escherichia coli, Pseudomonas aeruginosa, Bordetella pertussis, Moraxella catarrhalis, Coxiella burnetii, Chlamydophila pneumoniae, Mycoplasma pneumonia, Legionella pneumophila*, the SARS virus, the hantavirus (which can progress to Hantavirus Pulmonary Syndrome (HPS)), the anthrax toxin which is a three-protein exotoxin secreted by virulent strains of the bacterium, *Bacillus anthracia*.

In various embodiments of the methods described herein, altering vascular permeability can treat a disease or condition selected from the group consisting of pulmonary edema, or edema associated with a brain tumor, brain swelling, plural effusion, pericardial effusion, and combinations thereof.

In various embodiments of the methods described herein, altering vascular permeability can treat ischemia, or an ischemic disease or condition. In certain embodiments, the ischemia condition can be ischemic stroke, myocardial infarction, ischemic heart disease, cerebral infarct, peripheral vascular disease, elephantiasis, lymphatic obstruction, or combinations thereof.

In various embodiments of the methods described herein, altering vascular permeability can treat a disease or condition selected from the group consisting of ascites associated with malignancies, physical injury, metastasis, systemic hypertension, Meigs' syndrome, nephrotic syndrome, liver disease, kidney disease, and combinations thereof.

In various embodiments of the methods described herein, altering vascular permeability can treat a symptom that is found in any of the disease or condition or infection or irritant exposure. For example, pulmonary edema.

Various embodiments of the invention provide for a method of treating vascular permeability, comprising administering a lysyl oxidase (LOX) inhibiting agent to a subject in need thereof. In various embodiments, the LOX inhibiting agent is BAPN, a LOX siRNA, a LOX activity-inhibiting antibody, a LOX activity inhibiting peptide, an expression vector, or a modified synthetic RNA encoding a molecule that inhibits LOX, or a microRNA capable of inhibiting LOX gene expression. In one embodiment, the molecule encoded by the modified synthetic RNA is a peptide or a protein. In one embodiment, the encoded peptide has at least 90% sequence homology with SEQ. ID. No: 1. In one embodiment, the encoded protein comprises a 10-20 contiguous amino acid sequence having at least 90% sequence homology with SEQ. ID. No: 1.

Various embodiments of the invention provide for a method for increasing extracellular matrix (ECM) cross-linking comprising administering a sensitizer drug and administering light energy.

In various embodiments of the methods described herein, the sensitizer drug is riboflavin and the light energy is ultraviolet light.

In various embodiments of the methods described herein, administering the light energy is via an endoscope or a catheter. In various embodiments, administering the light energy is via transdermal delivery. In various embodiments, administering the sensitizer drug is via intravenous, oral, parenteral, transdermal or aerosol delivery.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 1B depicts a graph showing the quantitation of the total discontinuous area of at least 10 fields (*, p<0.01). FIG. 1B depicts a graph showing endothelial cell-cell junctional integrity measured by TEER in the L-HMVE cells cultured on gels with different elasticity (n=8, *, p<0.05). All error bars are s.e.m.

FIG. 2A depicts ECM structure in the control v.s. BAPN or LOX DNA-treated mouse lungs. top; light (H & E-stained) micrographs showing ECM structure of decellularized lung treated with BAPN or LOX DNA (bar, 3 µm). 2nd; Immunofluorescence micrographs showing Collagen VI distribution in the control v.s. BAPN or LOX DNA-treated decellularized lung (bar, 4 µm). 3rd; birefringence (Picrosirius Red-stained) micrographs showing collagen structure of decellularized lung treated with BAPN or LOX DNA (bar, 3 µm). bottom; TEM images showing endothelial cell-cell junctional integrity in the lung treated with BAPN or LOX DNA (bar, 500 nm). Arrowheads show the region of cell-cell junctions. FIG. 2B depicts a graph showing LOX activity in blood in mice treated with LOX inhibitor BAPN (n=10, *, p<0.01). FIG. 2C depicts a graph showing lung stiffness measured by the tensile loading assay in the mice treated with BAPN, control DNA (con DNA, vector only), or LOX DNA (n=10, *, p<0.05). FIG. 2D depicts mRNA levels of LOX in mouse lungs treated with control DNA (con DNA, vector only) or LOX DNA (n=9, *, p<0.05). All error bars are s.e.m.

FIG. 3A depicts vascular permeability in mouse lungs treated with BAPN. Vascular permeability is detected by Evan's Blue dye leakage in the lungs treated with BAPN and extracted dye contents are quantified by measuring at 620 nm (n=9, *, p<0.05). FIG. 3B depicts vascular permeability in mouse lungs treated with control DNA (con DNA) or LOX DNA. Graph showing vascular permeability detected by Evan's Blue dye leakage in the lungs overexpressed with LOX DNA (n=9, *, p<0.05). FIG. 3C depicts a graph showing the total inflammatory cell count in BAL fluid from the lungs treated with BAPN, control DNA (con DNA), or LOX DNA detected by Wright-Giemsa staining (n=8, *, p<0.01, **, p<0.05).

FIG. 4A depicts vascular permeability detected by Evan's Blue dye leakage in mouse lungs treated with LPS for 2 days (n=10, *, p<0.01). FIG. 4B depicts a graph showing the whole lung stiffness of LPS-treated lungs (n=8, *, p<0.05). FIG. 4C depicts a graph showing LOX mRNA levels in LPS-treated lungs (n=10, *, p<0.01). FIG. 4D depicts a graph showing LOX activity in mouse lungs treated with LPS (n=10, *, p<0.05). FIG. 4E depicts immunoblots showing LOX, LOXL1, LOXL2 and b-actin protein levels in mouse lungs treated with LPS. Error bars represent s.e.m.

FIG. 5A: top; Light (H & E-stained) micrographs showing ECM structure of decellularized lung treated with LPS or in combination with BAPN (bar, 3 µm). middle; Immunofluorescence micrographs showing the collagen VI distribution in the lung treated with LPS or in combination with BAPN after decellularization (bar, 4 µm). bottom; birefringence (Picrosirius Red-stained) micrographs showing collagen structure in the lung treated with LPS or in combination with BAPN after decellularization (bar, 3 µm). FIGS. 5B-5D depict graphs showing endothelial permeability detected by Evan's Blue dye leakage in the lungs treated with LPS in combination with (FIG. 5B) BAPN (n=8, *, p<0.01), (FIG. 5C) control siRNA (con siRNA) or LOX siRNA (n=8, *, p<0.01, **, p<0.05), or (FIG. 5D) control IgG (con IgG) or LOX inhibitory Ab (n=6, *, p<0.01). All error bars are s.e.m.

FIGS. 6A-6B demonstrate that matrix elasticity controls the integrity of endothelial cell-cell junction Immunofluorescence micrographs were used to measure cell-cell junction structure by VE-cadherin staining and nuclei by DAPI staining in L-HMVE cells on gels of different elasticity coated with collagen I (FIG. 6A) or collagen IV (FIG. 6B) (bar, 5 µm). Arrowheads show the region where cell-cell junctions are disrupted. Graphs showing the quantitation of the total discontinuous area of at least 10 fields (*, p<0.01). All error bars are s.e.m.

FIGS. 7A-7B demonstrate that LOX regulates collagen structures in the lung in vivo. FIG. 7A depicts micrographs showing the lungs before and after decellularization. FIG. 7B depicts immunoblots showing LOX, LOXL1, LOXL2 and GAPDH protein levels in the control (con) v.s. LOX DNA or LOX siRNA-treated lung.

FIG. 8A depicts representative photographs of control v.s. BAPN-treated lung after washout of intravascular Evan's Blue dye with PBS for 10 min. FIG. 8B depicts a graph showing IL-1 and TNF-levels in the BAPN or LPS-treated mouse lungs (n=8, *, p<0.01). All error bars are s.e.m.

FIG. 9A depicts graphs showing LOX activity in blood (upper) and lung stiffness (lower) in the mice treated with control (con) IgG or LOX inhibitory Ab (n=10, *, p<0.05). FIG. 9B, Left: Birefringence (Picrosirius Red-stained) micrographs showing collagen structure of decellularized lung treated with control (con) IgG or LOX inhibitory Ab (bar, 6 μm). Right: Graph showing endothelial permeability detected by Evan's Blue dye leakage in the lungs treated with control IgG or LOX inhibitory Ab (n=9, *, p<0.05). FIG. 9C depicts graphs showing LOX activity in blood (upper) and lung stiffness (lower) in the mice treated with control (con) siRNA or LOX siRNA (n=10, *, p<0.05). FIG. 9D: Left: Birefringence (Picrosirius Red-stained) micrographs showing collagen structure of decellularized lung treated with control (con) siRNA or LOX siRNA (bar, 3 μm). Right: Graph showing endothelial permeability detected by Evan's Blue dye leakage in the lungs treated with control (con) siRNA or LOX siRNA (n=9, *, p<0.05). All error bars are s.e.m.

DETAILED DESCRIPTION

Figures 1A, 1B:
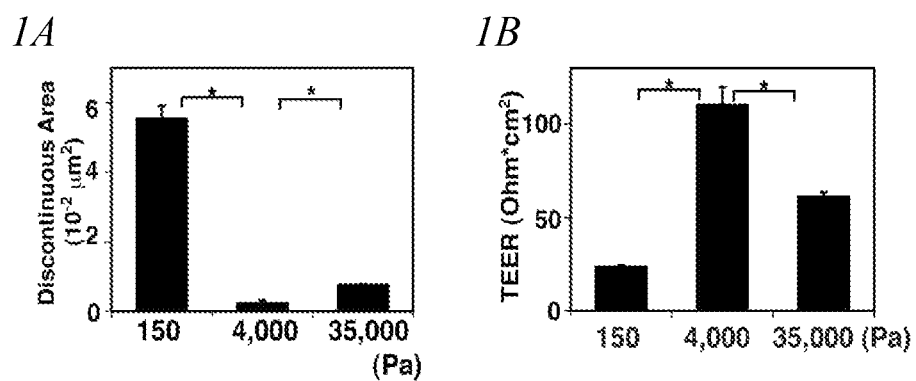
FIGS. 1A-1B demonstrate that matrix elasticity controls the integrity of endothelial cell-cell junction.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N. Y. 2001); March, *Advanced Organic Chemistry Reactions, Mechanisms and Structure* 5$^{th}$ ed., J. Wiley & Sons (New York, N. Y. 2001); and Sambrook and Russel, *Molecular Cloning: A Laboratory Manual* 3rd ed., Cold Spring Harbor Laboratory Press (Cold Spring Harbor, N. Y. 2001), provide one skilled in the art with a general guide to many of the terms used in the present application. For references on how to prepare antibodies, see D. Lane, *Antibodies: A Laboratory Manual* (Cold Spring Harbor Press, Cold Spring Harbor N.Y., 1988); Kohler and Milstein, (1976) Eur. J. Immunol 6: 511; Queen et al. U.S. Pat. No. 5,585,089; and Riechmann et al., Nature 332: 323 (1988).

One skilled in the art will recognize many methods and materials similar or equivalent to those described herein, which could be used in the practice of the present invention. Indeed, the present invention is in no way limited to the methods and materials described. For purposes of the present invention, various terms are defined herein.

Increased vascular permeability and pulmonary edema are prominent features of acute lung injury and ARDS, which are commonly assumed to be controlled by levels of critical soluble cytokines, such as VEGF and TNFα[7,8,11,12]. Here, the inventors show that changes of ECM structure and mechanics play an equally important role in control of vascular permeability and endotoxin-induced pulmonary edema. Strikingly, the potent effects of endotoxin on pulmonary vascular permeability can be prevented by manipulating ECM structure, and hence, this mechanical control pathway could potentially lead to new approaches to clinical therapy in the future, in addition to providing greater insight into how changes in pulmonary microvascular structure influence organ pathophysiology.

Changes in LOX activity levels that alter tissue structure and ECM mechanics contribute to many pathological processes that are characterized by abnormal vascular permeability, including fibrotic disorders [33,39] and cancer progression [13,37], as well as cardiovascular diseases [20,40,41]. The inventors' results show that ECM mechanics need to be regulated tightly to maintain optimal cell-cell junctional integrity and pulmonary vascular function in normal lung. Specifically, using various LOX inhibitors (BAPN, LOX specific inhibitory Ab, and LOX siRNA) as well as LOX over-expression, the inventors found that changes in ECM structural cross-linking and rigidity that deviate from the normal range (either too rigid or too flexible) result in increased vascular permeability in vivo, just as altering ECM mechanics does in vitro. LOX manipulation altered lung stiffness between 1000 to 2500 Pa, which resulted in changes in vascular permeability in the lung in vivo (FIG. 2). In contrast, while the inventors observed a similar qualitative permeability response to changes in stiffness within endothelial cells cultured on ECM gels, the absolute values of stiffness were very different (cell-cell junctions were disrupted on ECM gels with 150 Pa or 35,000 Pa). This is likely because of difference in the measurement tools the inventors utilized (rheology of cultured gels versus tensile loading of whole lung sections), which can produce different values of mechanical properties based on the area to which force is applied[42]. In addition, the inventors' in vitro studies employed only endothelial cells cultured on top of gels composed of one type of ECM component, whereas whole lung contains various cell types grown within three-dimensional ECMs composed of a complex array of insoluble ECM components and bound growth factors. In addition, lung epithelial and stromal cells secrete soluble factors and ECM proteins differently in response to changes in ECM mechanics, which might feedback to further alter ECM remodel and mechanics; changes in permeability in vivo also can result in fibrin deposition, which can further alter ECM stiffness. In any case, the inventors' studies show that endothelial cells exhibit a similar qualitative vascular permeability response to changes in mechanics in vitro and in vivo, much as the inventors previously showed for their angiogenic response to alterations in ECM stiffness [15]. These studies show that ECM mechanics and structural changes need to be regulated carefully to maintain optimal pulmonary vascular function in the lung in vivo, just as the inventors observed with cultured endothelial cells in vitro.

The inventors' studies have shown that ECM structure and elasticity control vascular permeability by altering formation of both VE-cadherin-containing adherens junctions and tight junctions [43]. The mechanism by which stiffness influences junctional integrity remains unclear; however, the localization of VE-cadherin is changed in a stiffness-dependent manner, with more VE-cadherin being present in the cytoplasm on more flexible substrates. One possible mechanism of control might involve the small GTPases, Rho and Rac, because ECM stiffness [44] and mechanical forces [45,46] control their activities, and Rho and Rac have been shown to regulate VE cadherin localization and cell-cell junctional integrity [47].

Because LOX can alter ECM structure in multiple ways through changing the expression or activities of various chemical factors that influence ECM metabolism (e.g., TGFb, MCP1 etc.)[48,49] it is possible that ECM components other than collagens and elastins also contribute to the effects the inventors observed. LOX inhibition also can render collagen more susceptible to degradation [50]; however, the inventors could not detect any change in collagen protein levels or degradation (measured by quantitating hydroxyproline levels) in BAPN treated mice. On the other hand, past studies have shown that even a partial inhibition of collagen cross-linking results in changes in aortic wall stiffness [51,52]. BAPN treatment appears to produce similar changes of ECM structure and mechanics in the lung via induction of partial inhibition of collagen cross-linking, and thereby increases pulmonary vascular permeability in the inventors' system.

LOX can increase production of reactive oxygen species, such as hydrogen peroxide, which can increase vascular permeability [53]. It is also possible that the collagen cross-linking modulating agents the inventors used could produce similar effects by inducing an inflammatory cascade. However, these agents did not change the levels of inflammatory cytokines in the lung. The inventors' finding that altering the stiffness of synthetic ECMs produces similar effects on junctional integrity and vascular permeability in vitro suggests that the effects of these agents on ECM mechanics represent the key control point for vascular barrier control. The inventors' results clearly show that these agents, even in a short treatment (2 weeks of BAPN treatment and 1 week with LOX DNA/siRNA), changed collagen structure, fiber alignment and thickness. Therefore, these treatments affect lung vascular endothelial cell-cell junctional integrity at least partly by inhibiting collagen crosslinking.

Mouse lungs treated with endotoxin LPS that exhibited greatly enhanced vascular permeability were much stiffer than non-treated lungs, suggesting that endotoxin might increase lung vascular leakage by altering ECM mechanics. However, leaky vessels might also release serum components that could, in turn, alter ECM structure; thus, this may involve a complex feedback loop in vivo. LPS rapidly enhances permeability and leukocyte extravasation, while ECM-stiffness mediated effects are more long term. Nevertheless, there is clear interplay between these chemical and structural changes in LPS-treated lungs because LOX inhibition restored the ability of LPS to increase vessel permeability. The variations in lung stiffness the inventors measured may not reflect microscale changes in ECM elasticity, and thus, it is difficult to relate local changes in ECM mechanics to specific variations in vascular permeability within distinct regions of the lung. Nevertheless, taken together, these data suggest that ECM mechanics represents a previously unrecognized control point for vascular permeability control.

In summary, these results demonstrate a novel mechanism for control of vascular permeability in which endothelial barrier function is regulated by changes in ECM mechanics mediated by LOX. This pathway also mediates the effects of endotoxin LPS on vascular leakage and pulmonary edema, which can be prevented by modulating LOX activity. LOX activity and resulting changes of ECM structure could therefore represent novel therapeutic targets for control of pulmonary edema, ARDS (e.g., induced by sepsis), and a range of other diseases caused by abnormal vascular permeability.

Embodiments of the present invention are based, at least in part, on these findings.

Various embodiments of the present invention provide for a method of altering vascular permeability in a tissue or organ, comprising: administering an agent that modulates the mechanical properties of the extracellular matrix (ECM) to a subject in need thereof. The mechanical properties of the ECM can be modulated to increase or decrease its stiffness, elastic recoil, viscoelasticity and the like by increasing or decreasing ECM production, deposition, cross-linking, alignment, prestress, or ECM degradation.

In various embodiments, the ECM, tissue, or organ mechanics of the subject is measured before treatment. This can be useful to determine whether agents to increase or agents to decrease ECM production, deposition, cross-linking, alignment, prestress, or ECM degradation are used. Measuring ECM mechanics can include measuring stiffness, elastic recoil, viscoelasticity, or combinations thereof. Measuring ECM, tissue, or organ mechanics can be done by clinical, optical imaging, or histopathological methods. Example of these methods include, but are not limited to atomic force microscopy, magnetic cytometry, rheometry, characterization of tissue stress-strain relationships. In some embodiments, the ECM mechanics can be measured by any method known to one skilled in the art. For example, as described in the Example section.

In certain embodiments, the agent administered modulates the mechanical properties of the ECM by altering ECM production, deposition, cross-linking, alignment, degradation, composition, surface topography, prestress, or combinations thereof.

Decreasing ECM Production, Deposition, Cross-Linking, Alignment, Prestress and Increasing ECM Degradation and Decreasing Stiffness or Rigidity In certain embodiments, the agent decreases the stiffness of the ECM when the tissue or organ has stiffness above a normal range for the tissue or organ.

In one embodiment of the methods described herein, the normal range for vascular permeability for a particular tissue or organ is the vascular permeability for the same particular tissue or organ from a healthy subject. For example, if the tissue is the lung, then the normal range of vascular permeability is obtained from the healthy lungs of a health subject. In other embodiments, the normal range is the vascular permeability for the same particular tissue or organ from the same subject, except the vascular permeability is from a non-disease portion of the tissue or organ. For example, if the tissue is the kidney, only one kidney is diseased with cancer, then the normal range of vascular permeability is obtained from the other healthy kidney of the same subject. In other embodiments, the normal range is the average vascular permeability for the same tissue or organ from a population of healthy subjects. In other embodiments, the normal range is the average plus one or two standard deviations of vascular permeability for the same tissue or organ from a population of healthy subjects. In some embodiments, the population of healthy subjects can range from at least three healthy individuals to 25 healthy individuals, and even more than 50 healthy individuals.

In certain embodiments, the agent, or an expression vector or a synthetic modified RNA encoding such agents, decreases ECM production, deposition, cross-linking, alignment, prestress, or combinations thereof, or increases ECM degradation, thereby decreasing tissue or organ stiffness. These agents and expression vector and synthetic, modified RNA encoding such agents are described in further detail herein.

In various embodiments, the agent is a proline analogue, a retinoid, an inhibitor of prolyl hydroxylase, an inhibitor of collagen cross-linking, an active collagen modulator, an angiostatic steroid or heparin. In various embodiments, the proline analogue is 1-azetidine-2-carboxylic acid, cis-hydroxyproline,d,L-3,4-dehydroproline, or thioproline. In various embodiments, the inhibitor of prolyl hydroxylase is alpha,alpha-dipyridyl.

In various embodiments, the inhibitor of collagen cross-linking is beta-aminopropionitrile (BAPN).

In various embodiments, the collagen modulator can be a matrix metalloproteinase (MMP) inhibitor, e.g. an agent that inhibits the expression and/or activity of one or more MMPs. In various embodiments, the MMP inhibitor can be a pan-MMP inhibitor. In various embodiments, the MMP inhibitor can be a specific MMP inhibitor. In various embodiments, a MMP inhibitor can be a small molecule, an inhibitory nucleic acid, and/or an antibody reagent.

The matrix metalloproteinase (MMPs) are a family of structurally-related zinc-containing endopeptidases which mediate the breakdown of connective tissue macro-molecules. The mammalian MMP family is composed of at least twenty enzymes, classically divided into four sub-groups based on substrate specificity and domain structure (Alexander & Werb, 1991; Murphy & Reynolds, 1993; Birkedal-Hansen, 1995). The sub-groups are the collagenases (such as MMP1, MMP8, MMP13), the stromelysins (such as MMP3, MMP10, MMP11), the gelatinases (such as MMP 2, MMP9) and the membrane-type MMPs (such as MMP14, MMP 15, MMP16, MMP17). Enzyme activity is normally regulated in vivo by tissue inhibitors of metalloproteinases (TIMPs).

Non-limiting examples of MMP inhibitors can include doxycycline (PERIOSTAT™); minocycline; TNP-470; marimastat; cipemastat; galardin; batimastat; MMI-270; MMI-166; tanomasttat; rebimastat; Ro 28-2653; 556052-30-3; 544678-85; 868368-30-3; and COL-3. Further discussion of MMP inhibitors can be found, e.g., in Fisher et al. 2006 Cancer metastasi Rev 25:115-136; Whittaker et al. 1999 Chem Rev 99:2735-2776; Pirard 2007 Drug Discovery Today 12:15-16; Jacobsen et al. BBA 2010 1803:72-94; Devy and Dransfield. Biochemistry Research International 2011 191670; U.S. Pat. Nos. 8,314,148; 7,504,537; 7,655,664; 8,507,670, 7,858,619; and International Patent Publications WO2014028334; WO2011023864; WO2011127532; WO2010007027; WO2009113736; WO2008065393; WO2009118292; each of which is incorporated by reference herein in its entirety.

Other collagen modulators are known in the art and can include, by way of non-limiting example, proline analogs (e.g., 1-azetidine-2-carboxylic acid, cis-hydroxyproline, d,L-3,4-dehydroproline, thioproline); inhibitors of prolyl hydroxylase (e.g., alpha,alpha-dipyridyl); Beta-aminopropionitrile; and beta-methyl d-xyloside; and retinoic acid (see, e.g., Ingber and Folkman. Laboratory Investigations 1988 59:44-51; which is incorporated by reference herein in its entirety).

In various embodiments, the agent that decreases ECM production, deposition, cross-linking, alignment, prestress, or increases ECM degradation, thereby decreasing tissue or organ stiffness is an agent that decreases lysyl oxidase (LOX) activity or expression.

In various embodiments, the agent that decreases LOX activity or expression is a LOX inhibitor.

In various embodiments, the LOX inhibitor is a micro-RNA (miRNA) capable of inhibiting LOX gene expression; BAPN; LOX siRNA; a molecule that inhibits LOX activity; a peptide that inhibits LOX activity; an antibody, or a fragment thereof, or an expression vector encoding a molecule that inhibits LOX. These miRNA, siRNA, peptdies, antibodies, and expression vectors are described in further detail herein.

In various embodiments, the peptide that inhibits LOX activity has the sequence EDTSCDYGYHRRFA (SEQ ID NO: 1), or fragments thereof.

In various embodiments, the antibody is a purified antibody that binds specifically to a 10-20, or a 6-12 amino acid polypeptide of a LOX protein, and inhibits LOX activity. In various embodiments, the LOX activity inhibiting antibody is a purified antibody that binds specifically to the sequence EDTSCDYGYHRRFA (SEQ ID NO: 1) or a sequence having at least 80, 85, 90, 95, 96, 97, 98, 99% identity, and inhibits LOX activity.

In various embodiments, the LOX activity inhibiting antibody is covalently bonded to a co-polymer. In various embodiments, the co-polymer is poly(D,L-lactide-co-glycolide)-block-poly(ethylene glycol).

In various embodiments, the agent is administered via an aerosol route, an intravenous route, a parenteral route or a transdermal route. In various embodiments, the agent is administered via aerosol delivery into the subject's lung. Additional routes of administration are described herein.

In various embodiments, the agent that decreases ECM production, deposition, cross-linking, alignment, prestress, or increases ECM degradation, thereby decreasing tissue or organ stiffness is a copper chelator. In various embodiments, an inhibitor of LOX activity or expression is a copper chelator. As used herein, "copper chelators" refers to an agent that can bind to copper, e.g. copper ions, and sequester them from LOX enzyme, thereby reducing the activity of LOX. In some embodiments, the copper chelator can preferentially chelate copper relative to other metal ions. In some embodiments, a copper chelators preferentially chelates copper at least 2×, at least 5×, at least 10×, or more relative to other metal ions.

Copper chelators are known in the art and can include, by way of non-limiting example, D-penicillamine; trientine (SYPRINE™ or TRIENTIN™); bis-8-aminoquinoline PA1637; Tetrathiomolybdate (TTM); ammonium tetrathiomolybdate; and clioquinol. Further information on copper chelators is available, e.g. in Ding et al., J Nutr Biochem 2011 22:301-310; Wadas et al. Current Pharmaceutical Design 2007 13:3-16; and International Patent Applications PCT/CA2001/001735; PCT/US2002/022951; and PCT/US2006/037268; and Canadian Patent Application 2828595; each of which is incorporated herein in its entirety.

In various embodiments, the LOX activity inhibiting antibody is covalently bonded to a co-polymer. In various embodiments, the co-polymer is poly(D,L-lactide-co-glycolide)-block-poly(ethylene glycol). In various embodiments, the LOX activity inhibiting antibody is covalently bonded to a nanoparticle.

In various embodiments, the agent is administered via an aerosol route, an intravenous route, a parenteral route or a transdermal route. In various embodiments, the agent is administered via aerosol delivery into the subject's lung. Additional routes of administration are described herein.

In some embodiments, multiple LOX inhibitors can be administered, e.g. BAPN and D-penicillamine can be administered to the same subject.

Increasing ECM Production, Deposition, Cross-linking, Alignment, Prestress, or Decreasing ECM Degradation; and Increasing Stiffness or Rigidity In various embodiments, an agent that increases the rigidity of the ECM when the tissue or organ has a stiffness below a normal range for the tissue or organ is administered.

In one embodiment of the methods described herein, the normal range for vascular permeability for a particular tissue or organ is the vascular permeability for the same particular tissue or organ from a healthy subject. For example, if the tissue is the lung, then the normal range of vascular permeability is obtained from the healthy lungs of a health subject. In other embodiments, the normal range is the vascular permeability for the same particular tissue or organ from the same subject, except the vascular permeability is from a non-disease portion of the tissue or organ. For example, if the tissue is the kidney, only one kidney is diseased with cancer, then the normal range of vascular permeability is obtained from the other healthy kidney of the same subject. In other embodiments, the normal range is the average vascular permeability for the same tissue or organ from a population of healthy subjects. In other embodiments, the normal range is the average plus one or two standard deviations of vascular permeability for the same tissue or organ from a population of healthy subjects. In some embodiments, the population of healthy subjects can range from at least three healthy individuals to 25 healthy individuals, and even more than 50 healthy individuals.

In various embodiments, the agent, or an expression vector or synthetic, modified RNA encoding such agents, increases ECM production, deposition, cross-linking, alignment, prestress, or combinations thereof, or decreases ECM degradation, thereby increasing tissue or organ stiffness. These agent, and expression vectors and synthetic, modified RNAs are described herein.

In various embodiments, the agent increases LOX activity or expression to increases the rigidity of the ECM, or to increases ECM production, deposition, cross-linking, alignment, prestress, or to decreases ECM degradation.

In various embodiments, the agent is an expression vector encoding a LOX, a fibronectin derived peptide, LOX enzyme, an enzyme that increases ECM cross-linking, an agent capable of glycosylating an ECM protein, an agent capable of post-translational modification of the ECM proteins, a microRNA capable of increasing LOX expression, a TGF-beta family member, an agent that increases production of an ECM molecule. These expression vectors, fibronectin derived peptides, and microRNAs are further described herein.

In various embodiments, the agent is a fibronectin derived peptide described in the International patent application entitled "Designing novel peptides for inducing fibronection matrix assembly" having the PCT International patent application number PCT/US2013/31193 filed Mar. 14, 2013, the contents of which are incorporated herein by reference in its entirety.

In various embodiments, the agent is any fibronectin derived peptide that is known in the art. For example, fibronectin derived peptides are described in Elizabeth Franco et al., "Fibronectin-Derived Fragments as Inducers of Adhesion and Chemotaxis of *Entamoeba histolytica* Trophozoites" 1997, The Journal of Infectious Diseases, 176: 1597-602; Fukai F. et al., Cell Mol Biol. 2000, 46:145-52; Kato R. et al., 2001, Experimental Cell Research, 265:54-63; Kato R. et al., 2002, Clin Cancer Res., 8:2455; and Ko J A. et al., 2008, Biochem Biophys Res Commun. June 6; 370(3):424-8.

In various embodiments, the agent is administered via an aerosol route, an intravenous route, a parenteral route or a transdermal route. In various embodiments, the agent is administered via aerosol delivery into the subject's lung. Additional routes of administration are described herein. In some embodiments, the agent is administering via a nebulizer. For example, the agent can be formulated as a powder for delivery via a nebulizer.

Treatment of Diseases and Conditions

Various embodiments of the invention provide for treatment of diseases and conditions by altering vascular permeability as described herein.

In various embodiments, altering vascular permeability treats a pulmonary disease or condition; for example, pulmonary edema, acute respiratory distress syndrome (ARDS), endotoxin-induced lung injury, pulmonary fibrosis, pulmonary embolism, pulmonary vascular hypertension, emphysema, pleural effusion, lung inflammation, sepsis.

In various embodiments, altering vascular permeability treats inflammation, or an inflammatory disease or condition; for example, arthritis, Crohn's disease, inflammatory bowel disease, Alzheimer's disease, diabetes, gout, atherosclerosis, vasculitis, infection, sepsis.

In various embodiments, altering vascular permeability treats a primary or metastatic cancer; for example, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

In various embodiments, altering vascular permeability treats an aberrant response to a chemical therapy, such as, IL-2 and interferon-alpha therapy.

In various embodiments, altering vascular permeability treats a disease or condition cause by an airborne toxicant; for example, diseases or conditions cause by smoke or other particulate inhalation or molecular or chemical inhalation.

In various embodiments, altering vascular permeability treats a diseases or conditions such as, pulmonary edema, or edema associated with a brain tumor, brain swelling, plural effusion, pericardial effusion.

In various embodiments, altering vascular permeability treats ischemia, or an ischemic disease or condition; for example, ischemic stroke, myocardial infarction, ischemic heart disease, cerebral infarct, peripheral vascular disease, elephantiasis, lymphatic obstruction.

In various embodiments, altering vascular permeability treats a disease or condition, such as ascites associated with malignancies, physical injury, metastasis, systemic hypertension, Meigs' syndrome, nephrotic syndrome, liver disease, kidney disease.

Various embodiments of the present invention provide for a method of treating vascular permeability, comprising administering a lysyl oxidase (LOX) inhibiting agent to a subject in need thereof.

In various embodiments, the LOX inhibiting agent in BAPN, a LOX siRNA, a LOX activity inhibiting antibody, a LOX activity inhibiting peptide, an expression vector or a modified synthetic RNA encoding a molecule that inhibits LOX, or a microRNA capable of inhibiting LOX gene expression. These LOX inhibiting agents are described herein.

Enhance Delivery and/or Effectiveness of Drug

Various embodiments of the present invention provide for enhancing delivery and/or effectiveness of a drug by administering an agent that alters vascular permeability to a subject in need thereof. In various embodiments, the drug is an anti-cancer drug. The agent that alters vascular permeability can be delivered prior to, concurrently with, or after the administration of the drug for which the delivery and/or effectiveness is to be enhanced.

Examples of anti-cancer drugs include, but are not limited to platinum chemotherapeutic agents, such as cisplatin, carboplatin, oxaliplatin, nedaplatin, and iproplatin. Other examples of anti-cancer drugs include, but are not limited to cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: treosulfan, and trofosfamide; plant alkaloids: vinblastine, paclitaxel, docetaxol; DNA topoisomerase inhibitors: doxorubicin, epirubicin, etoposide, camptothecin, topotecan, irinotecan, teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.); hormonal therapeutic treatments, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

Sensitizer Dug and Light Energy

Various embodiments of the present invention provide for a method for increasing extracellular matrix (ECM) cross-linking comprising: administering a sensitizer drug; and administering light energy.

In various embodiments, the sensitizer drug is riboflavin and the light energy is ultraviolet light.

In various embodiments, administering the light energy is via an endoscope or a catheter. In various embodiments, administering the light energy is via transdermal delivery. In various embodiments, administering the sensitizer drug is via intravenous, oral, parenteral, transdermal or aerosol delivery. Other modes of administrations are described herein.

Generation of LOX Modulating Peptides and Proteins

In some embodiments, synthetic, modified RNAs encoding a LOX modulating protein, peptide or fragment thereof, or encoding an ECM mechanical property modulating protein, peptide or fragment thereof, are administered to the subject to produce the proteins, peptides, or fragments in vivo.

As used herein, the terms "synthetic, modified RNA" or "modified RNA" or "modified mRNA" refer to an RNA molecule produced in vitro which comprises at least one modified nucleoside as that term is defined herein below. The modified mRNAs do not encompass mRNAs that are isolated from natural sources such as cells, tissue, organs etc., having those modifications, but rather only synthetic, modified RNAs that are synthesized using in vitro techniques, as described herein. The term "composition," as applied to the terms "synthetic, modified RNA" or "modified RNA," encompasses a plurality of different synthetic, modified RNA molecules (e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 75, at least 90, at least 100 synthetic, modified RNA molecules or more). In some embodiments, a synthetic, modified RNA composition can further comprise other agents (e.g., an inhibitor of interferon expression or activity, a transfection reagent, etc.). Such a plurality can include synthetic, modified RNA of different sequences (e.g., coding for different polypeptides), synthetic, modified RNAs of the same sequence with differing modifications, or any combination thereof.

As used herein the term "modified ribonucleoside" refers to a ribonucleoside that encompasses modification(s) relative to the standard guanine (G), adenine (A), cytosine (C), and uracil (U) nucleosides. Such modifications can include, for example, modifications normally introduced post-transcriptionally to mammalian cell mRNA, and artificial chemical modifications, as known to one of skill in the art.

As used herein the term "modified nucleoside" refers to a ribonucleoside that encompasses modification(s) relative to the standard guanine (G), adenine (A), cytidine (C), and uridine (U) nucleosides. Such modifications can include, for example, modifications normally introduced post-transcriptionally to mammalian cell mRNA, and artificial chemical modifications, as known to one of skill in the art.

Modified nucleosides include other synthetic and natural nucleobases such as inosine, xanthine, hypoxanthine, nubularine, isoguanisine, tubercidine, 2-(halo)adenine, 2-(alkyl)adenine, 2-(propyl)adenine, 2 (amino)adenine, 2-(aminoalkyll)adenine, 2 (aminopropyl)adenine, 2 (methylthio) N6 (isopentenyl)adenine, 6 (alkyl)adenine, 6 (methyl)adenine, 7 (deaza)adenine, 8 (alkenyl)adenine, 8-(alkyl)adenine, 8 (alkynyl)adenine, 8 (amino)adenine, 8-(halo)adenine, 8-(hydroxyl)adenine, 8 (thioalkyl)adenine, 8-(thiol)adenine, N6-(isopentyl)adenine, N6 (methyl)adenine, N6,N6 (dimethyl) adenine, 2-(alkyl)guanine, 2 (propyl)guanine, 6-(alkyl) guanine, 6 (methyl)guanine, 7 (alkyl)guanine, 7 (methyl) guanine, 7 (deaza)guanine, 8 (alkyl)guanine, 8-(alkenyl) guanine, 8 (alkynyl)guanine, 8-(amino)guanine, 8 (halo) guanine, 8-(hydroxyl)guanine, 8 (thioalkyl)guanine, 8-(thiol)guanine, N (methyl)guanine, 2-(thio)cytosine, 3 (deaza) 5 (aza)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl)cytosine, 5 (propynyl) cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl) uracil, 5 (guanidiniumalkyl)uracil, 5 (1,3-diazole-1-alkyl) uracil, 5-(cyanoalkyl)uracil, 5-(dialkylaminoalkyl)uracil, 5 (dimethylaminoalkyl)uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo) uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl) pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio) pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio) pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 (aminocarbonylethylenyl)-2,4-(dithio)pseudouracil, 1 (aminoalkylaminocarbonylethylenyl)-pseudouracil, 1 (aminoalkylamino-carbonylethylenyl)-2(thio)-pseudouracil, 1 (aminoalkylaminocarbonylethylenyl)-4 (thio)pseudouracil, 1 (aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino)purine, 5 substituted pyrimidines, N2-substituted purines, N6-substituted purines, O6-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof.

U.S. Patent Publication No. 2012/0046346 and Warren et al., Highly Efficient Reprogramming to Pluripotency and Directed Differentiation of Human Cells with Synthetic Modified mRNA, CELL STEM CELL 7, 618-630, Nov. 5, 2010, provide further discussion and examples of synthetic, modified DNA.

In some embodiments, protein coding nucleic acid sequences of a LOX modulating protein, peptide or fragment thereof or an ECM mechanical property modulating protein, peptide or fragment thereof, can be amplified by polymerase chain reaction (PCR) and cloned into protein expression vectors. The resultant expression vectors can be then be transfected into corresponding host for protein expression.

In one embodiment, the template DNA for PCR of a LOX coding sequence is a nucleic acid sequence that encodes a LOX protein. The template DNA is that of the human LOX gene found on chromosome 5 (5q23.3-31.2) in GENBANK™ Accession No: NG_008722.1; the human lysyl oxidase (LOX), transcript variant 2 mRNA in GENBANK™ Accession No: NM_001178102.1; and the transcript variant 1 mRNA in GENBANK™ Accession No: NM_002317.5.

The human LOX gene DNA sequence encodes a polypeptide of 417 amino acids, the first 21 residues of which constitute a signal peptide, with a weight of approximately 32 kDa. The carboxy terminus contains the active copper (II) ion, lysine, tyrosine, and cysteine residues that comprise the catalytically active site.

Lysyl oxidase is an extracellular copper enzyme that catalyzes formation of aldehydes from lysine residues in collagen and elastin precursors. These aldehydes are highly reactive, and undergo spontaneous chemical reactions with other lysyl oxidase-derived aldehyde residues, or with unmodified lysine residues. This results in cross-linking collagen and elastin, which is essential for stabilization of collagen fibrils and for the integrity and elasticity of mature elastin. Complex cross-links are formed in collagen (pyridinolines derived from three lysine residues) and in elastin (desmosines derived from four lysine residues) that differ in structure.

The importance of lysyl oxidase-derived cross-linking was established from animal studies in which lysyl oxidase was inhibited either by nutritional copper-deficiency or by supplementation of diets with β-aminopropionitrile (BAPN), an inhibitor of lysyl oxidase. This resulted in lathyrism, characterized by poor bone formation and strength, hyperextensible skin, weak ligaments, and increased occurrence of aortic aneurysms. These abnormalities correlated well with decreased cross-linking of collagen and elastin.

Examples of expression vectors and host cells are the pET vectors (NOVAGEN®), pGEX vectors (GE Life Sciences), and pMAL vectors (New England labs. Inc.) for protein expression in E. coli host cell such as BL21, BL21(DE3) and AD494(DE3)pLysS, Rosetta (DE3), and Origami(DE3) ((NOVAGEN®); the strong CMV promoter-based pcDNA3.1 (INVITROGEN™ Inc.) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (CLONTECH®), pAd/CMV/V5-

DEST, pAd-DEST vector (INVITROGEN™ Inc.) for adenovirus-mediated gene transfer and expression in mammalian cells; pLNCX2, pLXSN, and pLAPSN retrovirus vectors for use with the RETRO-X™ system from Clontech for retroviral-mediated gene transfer and expression in mammalian cells; pLenti4/V5-DEST™, pLenti6N5-DEST™, and pLenti6.2/V5-GW/lacZ (INVITROGEN™ Inc.) for lentivirus-mediated gene transfer and expression in mammalian cells; adenovirus-associated virus expression vectors such as pAAV-MCS, pAAV-IRES-hrGFP, and pAAV-RC vector (STRATAGENE®) for adeno-associated virus-mediated gene transfer and expression in mammalian cells; BACpak6 baculovirus (CLONTECH®) and pFast-Bac™ HT (INVITROGEN™ Inc.) for the expression in *Spodopera frugiperda* 9 (Sf9) and Sf11 insect cell lines; pMT/BiP/V5-His (INVITROGEN™ Inc.) for the expression in *Drosophila schneider* S2 cells; *Pichia* expression vectors pPICZα, pPICZ, pFLDα and pFLD (INVITROGEN™ Inc.) for expression in *Pichia pastoris* and vectors pMETα and pMET for expression in *P. methanolica*; pYES2/GS and pYD1 (INVITROGEN™ Inc.) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol Med. 94:191-5. Foreign heterologous coding sequences are inserted into the genome of the nucleus, chloroplast and mitochodria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. Biolistic gene gun method is used to introduce the vector in the algae. Upon its entry into chloroplasts, the foreign DNA is released from the gene gun particles and integrates into the chloroplast genome through homologous recombination.

In various embodiments, the expression vector is a viral vector, such as a lentivirus, adenovirus, or adeno-associated virus. A simplified system for generating recombinant adenoviruses is presented by He T C. et al. Proc. Natl. Acad. Sci. USA, 95:2509-2514, 1998. The gene of interest is first cloned into a shuttle vector, e.g. pAdTrack-CMV. The resultant plasmid is linearized by digesting with restriction endonuclease Pme I, and subsequently cotransformed into *E. coli* BJ5183 cells with an adenoviral backbone plasmid, e. g. pAdEasy-1 of STRATAGENE®'s ADEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenoviruses are generated within the HEK 293 cells.

In various embodiments, the viral vector is a lentiviral vector and there are many examples of use of lentiviral vectors for gene therapy and these references are hereby incorporated by reference (Klein, C. and Baum, C. (2004), Hematol. J., 5:103-111; Zufferey, R et. al. (1997), Nat. Biotechnol., 15:871-875; Morizono, K. et al. (2005), Nat. Med., 11:346-352; Di Domenico, C. et. al. (2005). Hum. Gene Ther., 16:81-90). The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with VIRAPOWER™ Lentiviral Expression systems from INVITROGEN™ Inc.

In various embodiments, the expression viral vector can be a recombinant adeno-associated virus (rAAV) vector. Using rAAV vectors, genes can be delivered into a wide range of host cells including many different human and non-human cell lines or tissues. Because AAV is non-pathogenic and does not illicit an immune response, a multitude of pre-clinical studies have reported excellent safety profiles. rAAVs are capable of transducing a broad range of cell types and transduction is not dependent on active host cell division. High titers, >$10^8$ viral particle/ml, are easily obtained in the supernatant and $10^{11}$-$10^{12}$ viral particle/ml with further concentration. The transgene is integrated into the host genome so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, the development of novel injection techniques into the brain, specifically convection enhanced delivery (CED; Bobo et al (1994), PNAS 91(6):2076-80; Nguyen et al. (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying the chimeric DNA coding sequence, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Generating LOX Inhibiting Antibodies

In some embodiments, the agent that modulates the mechanical properties of the ECM is an antibody that inhibits the enzyme activity of LOX. Hence the antibody is an inhibiting antibody. Such antibodies can be produced against the LOX protein using the LOX protein as the antigen. In some embodiments, the LOX protein for antibody production is protein sequence found in GENBANK™ Accession No: NP_002308.2 or NP_001171573.1. In some embodiments, a recombinantly synthesized LOX protein is used as the antigen for generation antibodies against LOX.

The protein encoded by the LOX gene is an extracellular copper enzyme that initiates the crosslinking of collagens and elastin. The enzyme catalyzes oxidative deamination of the epsilon-amino group in certain lysine and hydroxylysine residues of collagens and lysine residues of elastin. In addition to crosslinking extracellular matrix proteins, the encoded protein may have a role in tumor suppression. Defects in this gene are a cause of autosomal recessive cutis laxa type I (CL type I). Two transcript variants encoding different isoforms have been found for this gene.

In some embodiments, functional fragments of the inhibiting antibody to LOX are also contemplated. As used herein, in some embodiments, fragments of antibodies would be small portions of the whole antibody. By "functional", it is meant that the fragment can also inhibit the enzyme activity of LOX. The enzyme activity of LOX can be assayed by any method known in the art, for example, as it is described in the Example section. Accordingly, antibodies and fragments thereof that are produced against LOX, ie., that the antibodies and fragments do bind to LOX, will also be tested for inhibiting activity against the enzyme activity of LOX.

As used herein, the term "antibody" refers to immunoglobulin molecules and immunologically active portions of immunoglobulin molecules, i.e., molecules that contain an antigen binding site that immunospecifically binds an antigen. The terms also refers to antibodies comprised of two immunoglobulin heavy chains and two immunoglobulin light chains as well as a variety of forms besides antibodies; including, for example, Fv, Fab, and F(ab)'$_2$ as well as bifunctional hybrid antibodies (e.g., Lanzavecchia et al., Eur. J. Immunol 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2nd ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference.).

In various embodiments, the LOX inhibiting antibody is a polyclonal antibody. In one embodiment, the LOX inhibiting antibody is a monoclonal antibody. In various embodiments, the LOX inhibiting antibody is a humanized antibody. In various embodiments embodiment the LOX inhibiting antibody is a chimeric antibody. In various embodiments, the LOX inhibiting antibodies include, but are not limited to multispecific, human, single chain antibodies, Fab fragments, F(ab)'$_2$ fragments, fragments produced by a Fab expression library, domain-deleted antibodies (including, e.g., CH2 domain-deleted antibodies), anti-idiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Encompassed in the methods disclosed herein are LOX inhibiting antibodies that are, but are not limited to, engineered forms of antibodies and antibody fragments such as diabodies, triabodies, tetrabodies, and higher multimers of scFvs, single-domain antibodies, as well as minibodies, such as two scFv fragments joined by two constant (C) domains. See, e.g., Hudson, P. J. and Couriau, C., Nature Med. 9: 129-134 (2003); U.S. Publication No. 20030148409; U.S. Pat. No. 5,837,242.

In various embodiments, the LOX inhibiting antibodies can be obtained from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

In various embodiments for use in humans, the LOX inhibiting antibodies are human or humanized antigen-binding antibody fragments of the present invention and include, but are not limited to, Fab, Fab and F(ab)'$_2$, Fd, single-chain Fvs (scFv), single-domain antibodies, triabodies, tetrabodies, minibodies, domain-deleted antibodies, single-chain antibodies, disulfide-linked Fvs (sdFv) and fragments comprising either a variable light chain (VL) or variable heavy chain VH region. Antigen-binding antibody fragments, including single-chain antibodies, may comprise the variable region(s) alone or in combination with the entirety or a portion of the following: hinge region, CHI, CH2, and CH3 domains. Also included in the invention are antigen-binding fragments also comprising any combination of variable region(s) with a hinge region, CH1, CH2, and CH3 domains.

In various embodiments, antibodies in the therapeutic methods of the invention are those containing a deletion of the CH2 domain.

As used herein, the term "humanized" immunoglobulin or "humanized" antibody refers to an immunoglobulin comprising a human framework, at least one complementarity determining regions (CDR) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. For example, a humanized immunoglobulin would not encompass a chimeric mouse variable region/human constant region antibody.

As used herein, the term "framework region" refers to those portions of antibody light and heavy chain variable regions that are relatively conserved (i.e., other than the CDRs) among different immunoglobulins in a single species, as defined by Kabat, et al., op. cit. As used herein, a "human framework region" is a framework region that is substantially identical (about 85% or more) to the framework region of a naturally occurring human antibody.

As used herein, the term "chimeric" antibody refers to an antibody whose heavy and light chains have been constructed, typically by genetic engineering, from immunoglobulin gene segments belonging to different species. For example, the variable (V) segments of the genes from a mouse monoclonal antibody may be joined to human constant (C) segments, such as gamma1 and/or gamma4. A typical therapeutic or diagnostic chimeric antibody is thus a hybrid protein comprising at least one V region (e.g., VH or VL) or the entire antigen-binding domain (i.e., VH and VL) from a mouse antibody and at least one C (effector) region (e.g., CH (CH1, CH2, CH3, or CH4) or CL or the entire C domain (i.e., CH and CL) from a human antibody, although other mammalian species may be used. In some embodiments, especially for use in the therapeutic methods of the LOX inhibiting antibodies should contain no CH2 domain.

In various embodiments, a chimeric antibody may contain at least the LOX antigen binding Fab or F(ab)'$_2$ region while the humanized antibody can contain at least the LOX antigen binding Fv region fused to a human Fc region.

The terms "antigen" is well understood in the art and refer to the portion of a macromolecule which is specifically recognized by a component of the immune system, e.g., an antibody or a T-cell antigen receptor. The term antigen includes any protein determinant capable of specific binding to an immunoglobulin. Antigenic determinants usually consist of chemically active surface groupings of molecules such as amino acids or sugar side chains and usually have specific three dimensional structural characteristics, as well as specific charge characteristics.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

Recombinant expression of an antibody disclosed herein, or fragment, derivative or analog thereof, (e.g., a heavy or light chain of an antibody of the invention or a single chain antibody of the invention), including a recombinant protein derived from the antibody antigen-binding region, requires construction of an expression vector containing a polynucleotide that encodes the antibody. Once a polynucleotide encoding an antibody molecule or a heavy or light chain of an antibody or portion thereof (preferably containing the heavy or light chain variable domain) of the invention has been obtained, the vector for the production of the antibody molecule may be produced by recombinant DNA technology using techniques well known in the art. Thus, methods for preparing a protein by expressing a polynucleotide containing an antibody-encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT publication WO 86/05807; PCT publication WO 89/01036; and U.S. Pat. No. 5,122,464) and the variable domain of the antibody may be cloned into such a vector for expression of the entire heavy or light chain. Methods for generating multivalent and bispecific antibody fragments are described by Tomlinson I. and Holliger P. (2000) Methods Enzymol, 326, 461-479 and the engineering of antibody fragments and the rise of single-domain antibodies is described by Holliger P. (2005) Nat. Biotechnol. September; 23(9):1126-36, and are both hereby incorporated by reference.

Inhibition of LOX Expression

In various embodiments, the expression of LOX is inhibited by an RNA interference molecule. For example, LOX siRNA (h): sc-45218 from Santa CRUZ BIOTECHNOLOGY, INC.

Alternatively, RNA interference molecules can be determined using computer software programs and the gene of LOX. The human LOX gene found on chromosome 5 (5q23.3-31.2) in GENBANK™ Accession No: NG_008722.1; the human lysyl oxidase (LOX), transcript variant 2 mRNA in GENBANK™ Accession No: NM_001178102.1; and the transcript variant 1 mRNA in GENBANK™ Accession No: NM_002317.5.

Public access software programs and methods of predicting and selecting antisense oligonucleotides and siRNA are known in the art and are also found on the world wide web sites of GENSCRIPT™, AMBION®, DHARMACON™, OLIGOENGINE™, Wadsworth Bioinformatics Center, Whitehead Institute at the Massachusetts Institute of Technology and are also described in U.S. Pat. No. 6,060,248. After selecting the antisense oligonucleotides and siRNA sequences, these molecules can be produced biologically using an expression vector carrying the polynucleotides that encode the siRNA or antisense RNA. General molecular biological methods known in the art can be used to clone these sequences into the expression vectors. Examples of such are described herein.

RNA interference-inducing molecules include but are not limited to siRNA, dsRNA, stRNA, shRNA, microRNAi (mRNAi)/microRNA (miRNA), antisense oligonucleotides etc. and modified versions thereof, where the RNA interference molecule silences the gene expression of LOX. An anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. A siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent can be a cellular gene or genomic sequence, e.g. LOX. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence includes RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotides molecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

siRNAs useful for the methods described herein include siRNA molecules of about 15 to about 40 or about 15 to about 28 nucleotides in length, which are homologous to the LOX gene. Preferably, the LOX targeting siRNA molecules have a length of about 19 to about 25 nucleotides. More preferably, the targeting siRNA molecules have a length of about 19, 20, 21, or 22 nucleotides. The targeting siRNA molecules can also comprise a 3' hydroxyl group. The targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the LOX targeting RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the targeting RNA molecule is double stranded—one strand has a 3' overhang and the other strand can be blunt-ended or have an overhang. In the embodiment in which the targeting RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

Oligonucleotide Modifications

Unmodified oligonucleotides may be less than optimal in some applications, e.g., unmodified oligonucleotides can be prone to degradation by e.g., cellular nucleases. Nucleases can hydrolyze nucleic acid phosphodiester bonds. However, chemical modifications to one or more of the subunits of oligonucleotide can confer improved properties, and, e.g., can render oligonucleotides more stable to nucleases.

Modified nucleic acids and nucleotide surrogates can include one or more of:

(i) alteration, e.g., replacement, of one or both of the non-linking phosphate oxygens and/or of one or more of the linking phosphate oxygens in the phosphodiester backbone linkage.
(ii) alteration, e.g., replacement, of a constituent of the ribose sugar, e.g., of the 2' hydroxyl on the ribose sugar;
(iii) wholesale replacement of the phosphate moiety with "dephospho" linkers;
(iv) modification or replacement of a naturally occurring base with a non-natural base;
(v) replacement or modification of the ribose-phosphate backbone;
(vi) modification of the 3' end or 5' end of the oligonucleotide, e.g., removal, modification or replacement of a terminal phosphate group or conjugation of a moiety, e.g., a fluorescently labeled moiety, to either the 3' or 5' end of oligonucleotide; and
(vii) modification of the sugar (e.g., six membered rings).

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications may be incorporated in a single oligonucleotide or even at a single nucleoside within an oligonucleotide.

In some cases the modification will occur at all of the subject positions in the oligonucleotide but in many, and in fact in most cases it will not. By way of example, a modification may only occur at a 3' or 5' terminal position, may only occur in the internal region, may only occur in a terminal regions, e.g. at a position on a terminal nucleotide or in the last 2, 3, 4, 5, or 10 nucleotides of an oligonucleotide. A modification may occur in a double strand region, a single strand region, or in both. A modification may occur only in the double strand region of an oligonucleotide or may only occur in a single strand region of an oligonucleotide. E.g., a phosphorothioate modification at a non-bridging oxygen position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is particularly preferred, e.g., to enhance stability, to include particular nucleobases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Specific Modifications to Oligonucleotide
The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. In certain embodiments, one of the non-bridging phosphate oxygen atoms in the phosphate backbone moiety can be replaced by any of the following: S, Se, $BR_3$ (R is hydrogen, alkyl, aryl), C (i.e. an alkyl group, an aryl group, etc. . . . ), H, $NR_2$ (R is hydrogen, alkyl, aryl), or OR (R is alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotides diastereomers. Thus, while not wishing to be bound by theory, modifications to both non-bridging oxygens, which eliminate the chiral center, e.g. phosphorodithioate formation, may be desirable in that they cannot produce diastereomer mixtures. Thus, the non-bridging oxygens can be independently any one of S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is preferred. When the bridging oxygen is the 5'-oxygen of a nucleoside, replacement with nitrogen is preferred.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Modified phosphate linkages where at least one of the oxygens linked to the phosphate has been replaced or the phosphate group has been replaced by a non-phosphorous group, are also referred to as "non-phosphodiester backbone linkage."

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine and peptide nucleic acid (PNA) nucleoside surrogates. A preferred surrogate is a PNA surrogate.

Sugar Modifications

An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-AMINE (AMINE=NH$_2$; alkylamino, dialkylamino, heterocyclyl, arylamino, diaryl amino, heteroaryl amino, or diheteroaryl amino, ethylene diamine, polyamino) and aminoalkoxy, O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino) It is noteworthy that oligonucleotides containing only the methoxyethyl group (MOE), (OCH$_2$CH$_2$OCH$_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; thioalkyl; and alkyl, cycloalkyl, aryl, alkenyl and alkynyl, which may be optionally substituted with e.g., an amino functionality.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include "abasic" sugars, which lack a nucleobase at C-1'. These abasic sugars can also be further containing modifications at one or more of the constituent sugar atoms. Oligonucleotides can also contain one or more sugars that are in the L form, e.g. L-nucleosides.

Preferred substitutents are 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH2-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP) and 2'-O-dimethylaminoethyloxyethyl (2'-O-DMAEOE).

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. E.g., in preferred embodiments antisense strands of dsRNAs, are 5' phosphorylated or include a phosphoryl analog at the 5' prime terminus. 5'-phosphate modifications include those which are compatible with RISC mediated gene silencing. Modifications at the 5'-terminal end can also be useful in stimulating or inhibiting the immune system of a subject. Suitable modifications include: 5'-monophosphate ((HO)2(O)P—O-5'); 5'-diphosphate ((HO)$_2$(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5');

5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-beta-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-). Other embodiments include replacement of oxygen/sulfur with $BH_3$, $BH_3$— and/or Se.

Terminal modifications can also be useful for monitoring distribution, and in such cases the preferred groups to be added include fluorophores, e.g., fluorscein or an ALEXA® dye, e.g., ALEXA® 488. Terminal modifications can also be useful for enhancing uptake, useful modifications for this include cholesterol. Terminal modifications can also be useful for cross-linking an RNA agent to another moiety; modifications useful for this include mitomycin C.

Nucleobases

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-(halo)adenine, 2-(alkyl) adenine, 2-(propyl)adenine, 2 (amino)adenine, 2-(aminoalkyll)adenine, 2 (aminopropyl)adenine, 2 (methylthio) $N^6$ (isopentenyl)adenine, 6 (alkyl)adenine, 6 (methyl)adenine, 7 (deaza)adenine, 8 (alkenyl)adenine, 8-(alkyl)adenine, 8 (alkynyl)adenine, 8 (amino)adenine, 8-(halo)adenine, 8-(hydroxyl)adenine, 8 (thioalkyl)adenine, 8-(thiol)adenine, $N^6$-(isopentyl)adenine, $N^6$ (methyl)adenine, $N^6,N^6$ (dimethyl) adenine, 2-(alkyl)guanine, 2 (propyl)guanine, 6-(alkyl) guanine, 6 (methyl)guanine, 7 (alkyl)guanine, 7 (methyl) guanine, 7 (deaza)guanine, 8 (alkyl)guanine, 8-(alkenyl) guanine, 8 (alkynyl)guanine, 8-(amino)guanine, 8 (halo) guanine, 8-(hydroxyl)guanine, 8 (thioalkyl)guanine, 8-(thiol)guanine, N (methyl)guanine, 2-(thio)cytosine, 3 (deaza) 5 (aza)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl)cytosine, 5 (propynyl) cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl) uracil, 5 (guanidiniumalkyl)uracil, 5 (1,3-diazole-1-alkyl) uracil, 5-(cyanoalkyl)uracil, 5-(dialkylaminoalkyl)uracil, 5 (dimethylaminoalkyl)uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo) uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl) pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio) pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio) pseudouracil, 1 (aminocarbonylethylenyl)-pseudouracil, 1 (aminocarbonylethylenyl)-2-(thio)-pseudouracil, 1 (aminocarbonylethylenyl)-4 (thio)pseudouracil, 1 (aminocarbonylethylenyl)-2,4-(dithio)pseudouracil, 1 (aminoalkylaminocarbonylethylenyl)-pseudouracil, 1 (aminoalkylaminocarbonylethylenyl)-2(thio)-pseudouracil, 1 (aminoalkylaminocarbonylethylenyl)-4 (thio)pseudouracil, 1 (aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino)purine, 5 substituted pyrimidines, $N^2$-substituted purines, $N^6$-substituted purines, $O^6$-substituted purines, substituted 1,2,4-triazoles, or any O-alkylated or N-alkylated derivatives thereof;

Further purines and pyrimidines include those disclosed in U.S. Pat. No. 3,687,808, hereby incorporated by reference, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); or NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino) Placement within an oligonucleotide Some modifications may preferably be included on an oligonucleotide at a particular location, e.g., at an internal position of a strand, or on the 5' or 3' end of an oligonucleotide. A preferred location of a modification on an oligonucleotide, may confer preferred properties on the agent. For example, preferred locations of particular modifications may confer optimum gene silencing properties, or increased resistance to endonuclease or exonuclease activity.

One or more nucleotides of an oligonucleotide may have a 2'-5' linkage. One or more nucleotides of an oligonucleotide may have inverted linkages, e.g. 3'-3', 5'-5', 2'-2' or 2'-3' linkages.

An oligonucleotide may comprise at least one 5'-pyrimidine-purine-3' (5'-PyPu-3') dinucleotide wherein the pyrimidine is modified with a modification chosen independently from a group consisting of 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA) and 2'-O—CH$_2$CH$_2$-(4'-C) (ENA).

In one embodiment, the 5'-most pyrimidines in all occurrences of sequence motif 5'-pyrimidine-purine-3' (5'-PyPu-3') dinucleotide in the oligonucleotide are modified with a modification chosen from a group consisting of 2'''-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA) and 2'-O—CH$_2$CH$_2$-(4'-C) (ENA).

A double-stranded oligonucleotide may include at least one 5'-uridine-adenine-3' (5'-UA-3') dinucleotide wherein the uridine is a 2'-modified nucleotide, or a 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

General References

The oligoribonucleotides and oligoribonucleosides used in accordance with this invention may be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., Helv. Chim Acta, 1995, 78, 486-504; Beaucage, S. L. and Iyer, R. P., Tetrahedron, 1992, 48, 2223-2311 and Beaucage, S. L. and Iyer, R. P., Tetrahedron, 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. Nos. 5,256,775 or 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. J. Org. Chem. 2001, 66, 2789-2801. Preparation of sulfur bridged nucleotides is described in Sproat et al. Nucleosides Nucleotides 1988, 7,651 and Crosstick et al. Tetrahedron Lett. 1989, 30, 4693.

Sugar Group References

Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Helv. Chim Acta 1996, 79, 1930-1938), "LNA" (Wengel, J. Acc. Chem. Res. 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. Nucleic Acids Res. 1988, 16, 4583. Carbonate replacements are described in Tittensor, J. R. J. Chem. Soc. C 1971, 1933. Carboxymethyl replacements are described in Edge, M. D. et al. J. Chem. Soc. Perkin Trans. 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. Antisense and Nucleic Acid Drug Development 12, 103-128 (2002) and references therein.

Nucleobases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references are disclosed in the above section on base modifications Oligonucleotide Production The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art may additionally or alternatively be employed. It is also known to use similar techniques to prepare other oligonucleotides, such as the phosphorothioates, phosphorodithioates and alkylated derivatives. The double-stranded oligonucleotide compounds of the invention may be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotiode can then be resuspended in a solution appropriate for the intended formulation process.

Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Formulation and Administration

In one embodiment, the agent that modulates the mechanical properties of ECM is delivered in a pharmaceutically acceptable carrier in a therapeutically effective amount.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration. Additional carrier agents, such as liposomes, can be added to the pharmaceutically acceptable carrier.

As used herein, the term "a therapeutically effective amount" refers an amount sufficient to achieve the intended purpose. For example, an effective amount of a LOX modulator will cause a reduction or even completely halt vascular permeability. An effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

As used herein, the terms "administering," refers to the placement of an agent that modulates the mechanical properties of ECM to alter vascular permeability into a subject by a method or route which results in at least partial localization of the agent that modulates the mechanical properties of ECM at a desired site. The agent that modulates the mechanical properties of ECM can be administered by any appropriate route which results in an effective treatment in the subject. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

As used herein, the term "comprising" or "comprises" is used in reference to methods, and respective component(s) thereof, that are essential to the invention, yet open to the inclusion of unspecified elements, whether essential or not. The use of "comprising" indicates inclusion rather than limitation.

The term "consisting of" refers to methods, and respective components thereof as described herein, which are exclusive of any element not recited in that description of the embodiment.

Therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

Routes of administration include, but are not limited to aerosol, direct injection, intradermal, intravitreal, intramuscular, intraperitoneal, intravenous, subcutaneous, intranasal, epidural, oral, transmucosal, transdermal, or parenteral routes. "Parenteral" refers to a route of administration that is generally associated with injection, including but not limited to intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. The agent can be administered by any convenient route, and may be administered together with other biologically active agents. In various embodiments, the agent can be inhaled in to the lung via aerosol administration. Administration can be systemic or local.

The precise dose and formulation to be employed depends upon the potency of the agent, and include amounts large enough to produce the desired effect, e.g., a reduction in vascular permeability; for example, in the lung. The dosage should not be so large as to cause unacceptable adverse side effects. Generally, the dosage will vary with the type of agent that modulates the mechanical properties of ECM (e.g., an antibody or fragment, small molecule, siRNA, etc.), and with the age, condition, and sex of the patient are also considered. Dosage and formulation of the agent that modulates the mechanical properties of ECM will also depend on the route of administration, and the seriousness of the disease or disorder, and should be decided according to the judgment of the practitioner and each patient's circumstances. Effective doses can be extrapolated from dose-response curves derived from in vitro or animal model test systems.

In one embodiment, the agent that modulates the mechanical properties of the ECM is formulated for delivery by nebulizer. Such formulations are known in the art. For examples, nebulizer formulations are described in O'Riordan T G. et al., 2002, Respir Care. 47:1305-12; U.S. Patent publication US20070207091; and U.S. Pat. No. 7,405,207; the contents of which are incorporated by reference in their entirety.

The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 μg/kg body weight to 30 μg/kg body weight. Alternatively, the dose range will be titrated to maintain serum levels between 5 μg/mL and 30 μg/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

As exemplary, for the treatment of pulmonary edema, a LOX inhibitor and a pharmaceutically acceptable carrier can be formulated for aerosol application by inhalation the lung. The inhibitor can also be formulated for a transdermal delivery, e. g. a skin patch. For tissues and organs not so easily accessible, agent that modulates the mechanical properties of ECM can be administered to one of the main blood vessel that accesses the tissue or organ site.

In various embodiments, a LOX inhibitor is an RNA interference molecule such as an siRNA. Such siRNA is delivered by delivering a vector encoding small hairpin RNA (shRNA) in a pharmaceutically acceptable carrier to the cells in an organ of an individual. The shRNA is converted by the cells after transcription into siRNA capable of targeting LOX. In one embodiment, the vector can be a regulatable vector, such as tetracycline inducible vector. Such vectors with inducible promoters are well known in the art and are also easily found in the commercial sector, e. g. pSingle-tTS-shRNA vector from CLONTECH®.

In other embodiments, the treatment of vascular permeability-related diseases having localized aberrant vascular permeability, e.g. solid non-metastatic tumor, arthritis, comprises directly injecting an siRNA, dsRNA, or shRNA vector directed against a LOX gene to the location of tissue with aberrant vascular permeability.

In various embodiments, the RNA interfering molecules used in the methods described herein are taken up actively by cells in vivo following intravenous injection, e.g., hydrodynamic injection, without the use of a vector, illustrating efficient in vivo delivery of the RNA interfering molecules, e.g., the siRNAs used in the methods of the invention.

Other strategies for delivery of the RNA interfering molecules, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

In some embodiments, the siRNA, dsRNA, or shRNA vector directed against a LOX gene is administered intravenously, e. g. via central venous catheter (CVC or central venous line or central venous access catheter) placed into a large vein in the neck (internal jugular vein), chest (subclavian vein) or groin (femoral vein). Methods of systemic delivery of siRNA, dsRNA, or shRNA vector are well known in the art, e. g. as described herein and in Gao and Huang, 2008, (Mol. Pharmaceutics, Web publication December 30) and review by Rossil, 2006, Gene Therapy, 13:583-584. The siRNA, dsRNA, or shRNA vector can be formulated in various ways, e. g. conjugation of a cholesterol moiety to one of the strands of the siRNA duplex for systemic delivery to the liver and jejunum (Soutschek J. et. al. 2004, Nature, 432:173-178), complexing of siRNAs to protamine fused with an antibody fragment for receptor-mediated targeting of siRNAs (Song E, et al. 2005, Nat Biotechnol., 23: 709-717) and the use of a lipid bilayer system by Morrissey et al. 2005 (Nat Biotechnol., 23: 1002-1007). The lipid bilayer system produces biopolymers that are in the 120 nanometer diameter size range, and are labeled as SNALPs, for Stable-Nucleic-Acid-Lipid-Particles. The lipid combination protects the siRNAs from serum nucleases and allows cellular endosomal uptake and subsequent cytoplasmic release of the siRNAs (see WO/2006/007712). These references are incorporated by reference in their entirety.

In another embodiment, the treatment of vascular permeability-related diseases related to the lungs, e g pulmonary edema or ARDS, involves directly administering an agent that decreases the stiffness of the ECM into the lung via aerosol route, wherein the LOX function is the agent.

In other embodiments, the treatment of vascular permeability-related diseases having localized aberrant vascular permeability, e.g. solid non-metastatic tumor, arthritis, comprises directly injecting agent that modulates the mechanical properties of ECM into the location or tissue with aberrant vascular permeability, wherein the LOX function is blocked by the agent.

In some embodiments, the agent that modulates the mechanical properties of ECM can be targeted to specific organ or tissue by means of a targeting moiety, such as e.g., an antibody or targeted liposome technology. In some embodiments, a LOX inhibitor can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The conjugation of an antibody to a LOX inhibitor permits the inhibitor attached to accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

For therapeutic applications, the agent can be administered to a mammal, preferably a human, in a pharmaceutically acceptable dosage form, including those that may be administered to a human intravenously as a bolus or by continuous infusion over a period of time, by intramuscular, subcutaneous, intra-articular, intrasynovial, intrathecal, oral, topical, or inhalation routes. The agent is also suitably administered by intratumoral, peritumoral, intralesional, or perilesional routes, to exert local as well as systemic therapeutic effects.

In some embodiments, the agent is administered intravenously, e.g. via central venous catheter (CVC or central venous line or central venous access catheter) placed into a large vein in the neck (internal jugular vein), chest (subclavian vein) or groin (femoral vein).

Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, and sublingual tablets. The antibody will typically be formulated in such vehicles at a concentration of about 0.1 mg/ml to 100 mg/ml.

Depending on the type and severity of the disease, about 0.015 to 15 mg/kg of the agent is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful.

The effectiveness of the agent in treating the disease or condition can be improved by administering the agent serially or in combination with another agent that is effective for those purposes. Such other agents can be present in the composition being administered or can be administered separately. Also, the agent is suitably administered serially or in combination with radiological treatments, whether involving irradiation or administration of radioactive substances.

Efficacy testing can be performed during the course of treatment using the methods described herein. Measurements of the degree of severity of a number of symptoms associated with a particular ailment are noted prior to the start of a treatment and then at later specific time period after the start of the treatment.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

This invention is further illustrated by the following example which should not be construed as limiting the scope of the invention. To the extent that specific materials are mentioned, it is merely for purposes of illustration and is not intended to limit the invention. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

Some embodiments of the technology described herein can be defined according to any of the following numbered paragraphs:

1. A method of altering vascular permeability in a tissue or organ, comprising:
    administering an agent that modulates the mechanical properties of the extracellular matrix (ECM) to a subject in need thereof
2. The method of paragraphs 1, wherein the agent modulates the mechanical properties of the ECM by altering ECM production, deposition, cross-linking, alignment, degradation, composition, surface topography, prestress, or combinations thereof
3. The method of paragraph 1, further comprising measuring the ECM, tissue, or organ mechanics in the subject before treatment.
4. The method of paragraph 3, wherein measuring ECM mechanics comprises measuring stiffness, elastic recoil, viscoelasticity, or combinations thereof
5. The method of paragraphs 3-4, wherein measuring ECM, tissue, or organ mechanics is by clinical, optical imaging, histopathological or physical methods.
6. The method of paragraph 5, wherein the measuring methods comprise atomic force microscopy, magnetic cytometry, rheometry, characterization of tissue stress-strain relationships, or combinations thereof
7. The method of paragraphs 1-6, comprising administering an agent that decreases the stiffness of the ECM when the tissue or organ has stiffness above a normal range for the tissue or organ.
8. The method of paragraphs 1-7, wherein the agent decreases ECM production, deposition, cross-linking, alignment, prestress, or combinations thereof, or increases ECM degradation, or an expression vector or a synthetic modified RNA encoding such agents, thereby decreasing tissue or organ stiffness.
9. The method of paragraph 8, wherein the agent that decreases ECM deposition is a proline analogue, a retinoid, an inhibitor of prolyl hydroxylase, an inhibitor of collagen cross-linking, an active collagen modulator, an angiostatic steroid or heparin.
10. The method of paragraph 9, wherein the proline analogue is 1-azetidine-2-carboxylic acid, cis-hydroxyproline,d,L-3,4-dehydroproline, or thioproline.
11. The method of paragraph 9, wherein inhibitor of prolyl hydroxylase is alpha,alpha-dipyridyl.
12. The method of paragraph 9, wherein the inhibitor of collagen cross-linking is Beta-aminopropionitrile.
13. The method of paragraph 9, wherein the collagen modulator is selected from the group consisting of:
    a matrix metalloproteinase inhibitor; doxycycline; and TNP-470.
14. The method of paragraphs 1-10, wherein the agent decreases lysyl oxidase (LOX) activity or expression.
15. The method of paragraph 4, wherein the agent is a LOX inhibitor.
16. The method of paragraph 15, wherein the LOX inhibitor is a microRNA capable of inhibiting LOX gene expression.
17. The method of paragraph 15, wherein the LOX inhibitor is BAPN.
18. The method of paragraph 15, wherein the LOX inhibitor is a LOX siRNA
19. The method of paragraph 15, wherein the LOX inhibitor is a molecule that inhibits LOX activity.
20. The method of paragraph 15, wherein the LOX inhibitor is a peptide that inhibits LOX activity.
21. The method of paragraph 20, wherein the peptide has the sequence EDTSCDYGYHRRFA (SEQ ID NO: 1), or fragments thereof
22. The method of paragraph 15, wherein the LOX inhibitor is an antibody, or a fragment thereof
23. The method of paragraph 22, wherein the antibody is a purified antibody that binds specifically to a 10-20 amino acid polypeptide of a LOX protein.
24. The method of paragraph 22, wherein the antibody is a purified antibody that binds specifically to a 6-12 amino acid polypeptide of a LOX protein, and inhibits LOX activity.
25. The method of paragraph 22, wherein the LOX activity inhibiting antibody is a purified antibody that binds specifically to the sequence EDTSCDYGYHRRFA (SEQ ID NO: 1) or a sequence having at least 80% identity, and inhibits LOX activity.
26. The method of paragraph 22, wherein the LOX activity inhibiting antibody is covalently bonded to a co-polymer.
27. The method of paragraph 26, wherein the co-polymer is poly(D,L-lactide-co-glycolide)-block-poly(ethylene glycol).
28. The method of paragraph 22, wherein the LOX activity inhibiting antibody is covalently bonded to a nanoparticle.
29. The method of paragraph 15, wherein the LOX inhibitor is the expression vector encoding a nucleic acid or a protein or peptide that inhibits LOX.
30. The methods of any of paragraphs 1-15, wherein the agent is a copper chelator.
31. The method of paragraph 30, wherein the copper chelator is selected from the group consisting of:
    D-penicillamine; trientine; bis-8-aminoquinoline PA1637; Tetrathiomolybdate (TTM); ammonium tetrathiomolybdate; and clioquinol.
32. The method of any of paragraphs 30-31, wherein the copper chelator is covalently bonded to a co-polymer.
33. The method of paragraph 32, wherein the co-polymer is poly(D,L-lactide-co-glycolide)-block-poly(ethylene glycol).

34. The method of any of paragraphs 30-33, wherein the copper chelator is covalently bonded to a nanoparticle.
35. The method of paragraphs 1-6, comprising administering an agent that increases the rigidity of the ECM when the tissue or organ has a stiffness below a normal range for the tissue or organ.
36. The method of paragraph 1-7, wherein the agent increases ECM production, deposition, cross-linking, alignment, prestress, or combinations thereof, or decreases ECM degradation, or an expression vector or synthetic modified RNA encoding such agents, thereby increasing tissue or organ stiffness.
37. The method of paragraphs 35-36, wherein the agent increases LOX activity or expression.
38. The method of paragraph 317, wherein the agent is an expression vector encoding LOX.
39. The method of paragraph 37, wherein the agent is a fibronectin derived peptide.
40. The method of paragraph 37, wherein the agent is a LOX enzyme or an enzyme that increases ECM cross-linking.
41. The method of paragraph 36, wherein the agent is an agent capable of glycosylating an ECM protein or an agent capable of post-translational modification of the ECM protein.
42. The method of paragraph 37, wherein the agent is a microRNA capable of increasing LOX expression.
43. The method of paragraph 37, wherein the agent is a TGF-beta family member.
44. The method of paragraph 37, wherein the agent increases production of an ECM molecule.
45. The method of any one of the above paragraphs, wherein the agent is administered via an aerosol route, an intravenous route, a parenteral route or a transdermal route.
46. The method of any one of the above paragraphs, wherein the agent is administered via aerosol delivery into the subject's lung.
47. The method of paragraph 1, wherein altering vascular permeability treats a pulmonary disease or condition selected from the group consisting of pulmonary edema, acute respiratory distress syndrome (ARDS), endotoxin-induced lung injury, pulmonary fibrosis, pulmonary embolism, pulmonary vascular hypertension, emphysema, pleural effusion, lung inflammation, sepsis, and combinations thereof
48. The method of paragraph 1, wherein altering vascular permeability treats inflammation, or an inflammatory disease or condition selected from the group consisting of arthritis, Crohn's disease, inflammatory bowel disease, Alzheimer's disease, diabetes, gout, atherosclerosis, vasculitis, infection, sepsis, and combinations thereof
49. The method of paragraph 1, wherein altering vascular permeability treats a primary or metastatic cancer selected from the group consisting of breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.
50. The method of paragraph 1, wherein altering vascular permeability enhances delivery and/or effectiveness of a drug.
51. The method of paragraph 50, wherein the drug is an anti-cancer drug.
52. The method of paragraph 1, wherein altering vascular permeability treats an aberrant response to a chemical therapy.
53. The method of paragraph 52, wherein the chemical therapy is interferon-alpha or IL-2 therapy.
54. The method of paragraph 1, wherein altering vascular permeability treats a disease or condition cause by an airborne toxicant.
55. The method of paragraph 54, wherein the disease or condition cause by an airborne toxicant is caused by smoke or other particulate inhalation or molecular or chemical inhalation.
56. The method of paragraph 1, wherein altering vascular permeability treats a disease or condition or symptom cause by an infectious agent.
57. The method of paragraph 56, wherein the disease or condition or symptom cause by an infectious agent is caused by a virus, bacteria, fungus, parasite or toxin.
58. The method of paragraph 1, wherein altering vascular permeability treats a disease or condition selected from the group consisting of pulmonary edema, or edema associated with a brain tumor, brain swelling, plural effusion, pericardial effusion, and combinations thereof
59. The method of paragraph 1, wherein altering vascular permeability treats ischemia, or an ischemic disease or condition.
60. The method of paragraph 59, wherein the ischemia condition is ischemic stroke, myocardial infarction, ischemic heart disease, cerebral infarct, peripheral vascular disease, elephantiasis, lymphatic obstruction, or combinations thereof
61. The method of paragraph 1, wherein altering vascular permeability treats a disease or condition selected from the group consisting of ascites associated with malignancies, physical injury, metastasis, systemic hypertension, Meigs' syndrome, nephrotic syndrome, liver disease, kidney disease, and combinations thereof
62. A method of treating vascular permeability, comprising administering a lysyl oxidase (LOX) inhibiting agent to a subject in need thereof
63. The method of paragraph 62, wherein the LOX inhibiting agent is BAPN, a LOX siRNA, a LOX activity inhibiting antibody, a LOX activity inhibiting peptide, an expression vector, or a modified synthetic RNA encoding a molecule that inhibits LOX, a microRNA capable of inhibiting LOX gene expression; or a copper chelator.
64. A method for increasing extracellular matrix (ECM) cross-linking comprising:
administering a sensitizer drug; and
administering light energy.
65. The method of paragraph 64, wherein the sensitizer drug is riboflavin and the light energy is ultraviolet light.
66. The method of paragraph 64, wherein administering the light energy is via an endoscope or a catheter.
67. The method of paragraph 64, wherein administering the light energy is via transdermal delivery.
68. The method of paragraph 64, wherein administering the sensitizer drug is via intravenous, oral, parenteral, transdermal or aerosol delivery.

EXAMPLES

Example 1

Materials and Methods
Materials
Anti-CD31 and anti-VE cadherin monoclonal antibodies (1:100 for staining) were from Transduction laboratory (Lexington, Ky.). Anti-collagen I, III, IV, VI, LOX, LOXL1, and LOXL2 polyclonal antibodies (1:100 for staining and 1:1,000 for immunoblotting) were from Abcam. Anti-ZO1 polyclonal antibody (1:100 for staining) was from Invitrogen. Anti-β-actin monoclonal antibody (1:1,000 for immunoblotting) was from Sigma. Anti-GAPDH antibody (1:5,000 for immunoblotting) was from Millipore. LOX specific polyclonal inhibitory antibody was raised against the synthetic peptide of human/mouse LOX (EDTSCDY-GYHRRFA (SEQ ID NO:1)) (Genscript, Piscataway, N.J.)[13,36,37]. Mice treated with this LOX antibody exhibit reduced LOX activity and display significant decreases in LOX-mediated collagen crosslinking, as well as less linear collagen fibrils [13,36]. LPS and BAPN were from Sigma. L-HMVE cells (Lonza, Walkersville, Md.) were cultured in EBM-2 (Cambrex) supplemented with 5% fetal bovine serum (FBS) and growth factors according to the manufacturer's instructions[3].

Plasmid Construction and Gene Knockdown

The full length LOX plasmid was from Open Biosystems (Huntsville, Ala.) and subcloned into pOC mammalian expression vector. The inventors used pOC vector as a control. Gene knockdown was performed using the RNA interference technique [15]. siRNA for mouse LOX was 5'-CAACGGGCAGGUGUUCAG-3' (SEQ ID NO:2) and 5'-CUGAACACCUGCCCGUUG-3' (SEQ ID NO:3)[54]. As a control, siRNA duplex with irrelevant sequence (QIAGEN) was used.

Biochemical Methods

LOX activity in the serum and lung homogenate was measured using LOX activity assay kit (ABD Bioquest, CA) in which LOX substrate that releases hydrogen peroxide was detected [13,37,55]. Hydroxyproline in lung tissue or serum was measured using Hydroxyproline assay kit (Biovision, Milpitas, Calif.)[27]. The levels of IL-1 and TNF-α in the lung homogenate were measured by ELISA (R&D systems).

Molecular Biological Methods

Quantitative reverse transcription (qRT)-PCR was performed with the Quantitect SYBR Green RT-PCR kit (QIAGEN) using ABI 7300 real time PCR system (Applied Biosystems, Foster City, Calif.). Cyclophilin controlled for overall cDNA content. The primers used for mouse cyclophilin were forward; 5'-CAGACGCCACTGTCGCTTT-3' (SEQ ID NO:4), reverse; 5'-TGTCTTTGGAACTTTGTCT-GCAA-3'(SEQ ID NO:5)[15]. The primers for mouse LOX were forward; 5'-TCTTCTGCTGCGTGACAACC-3'(SEQ ID NO:6), reverse; 5'-GAGAAACCAGCTTGGAACCAG-3'(SEQ ID NO:7).

Cell Analysis Methods

L-HMVE cell monolayer junction formation was analyzed using immunohistochemistry with VE-cadherin antibody staining [15]. Flexible polyacrylamide gel culture substrates were prepared using mixture of the acrylamide and the bis-acrylamide [15] and coated with fibronectin (1 mg/cm$^2$), collagen-I and -IV (1 mg/cm$^2$). Substrate flexibility was controlled by varying the acrylamide (2-4%) and the bis-acrylamide (0.1-0.5%) concentration; the Young's modulus (stiffness) was determined using rheology [56]. L-HMVE cells were cultured for 12 h on the gels and immunostaining was performed and analyzed using confocal Leica SP2 microscope [15]. The integrity of the L-HMVE cell monolayer was evaluated by measuring TEER. In Transwell cultures, TEER was measured using a Millicell ERS meter (Millipore, Bedford, Mass.) coupled to a chopstick-like electrode, and TEER values (U×cm$^2$) were determined by subtracting the baseline resistance value measured in the absence of cells and then multiplying the remaining 'specific' resistance value (U) times the cell culture surface area (cm$^2$)[57].

In vivo Pulmonary Permeability Assay.

The in vivo animal study was carried out in strict accordance with the recommendations in the Guide for the Care and Use of Laboratory Animals of the National Institutes of Health. All animal studies were reviewed and approved by the Animal Care and Use Committee of Boston Children's Hospital. Mice (6-10 weeks old, CD1 strain, female) were treated with LPS (100 mg, intraperitoneally) and lung permeability was assessed 2 days after injection [3]. For gene knockdown or gene overexpression, delivery of siRNA and DNA into mice was performed using retro orbital injection of the mixture with jet PEI (PolyPlus) or Exgen (Fermentas) per the manufacturer's instructions, respectively [3,23,24,58]. Control DNA (vector only) and siRNA with irrelevant sequence were used as controls; these delivery methods have been shown not to elevate the serum levels of major pro-inflammatory cytokines (e.g., TNF-α, IL-6 etc.)[59]. Gene knockdown or overexpression in the lung (2 days later) was confirmed by measuring mRNA and/or protein levels using qRT-PCR and IB, respectively. The lung permeability was measured using Evan's Blue dye or low MW fluorescently labeled dextran (MW 4000, sigma) leakage [3]. Evans blue dye was extracted from the lung by incubation with formamide (70° C. for 24 h) and the concentration of Evans blue was estimated by dual-wavelength spectrophotometer (620 nm and 740 nm). Mice were treated with BAPN (3 mg/kg, drinking water) for 14 days [13]. The inventors also treated mice with LOX function-blocking polyclonal antibody (3 mg/kg)[13,36], LOX DNA or LOX siRNA (10 mg/mouse) injected intravenously (retro orbital injection) twice per week. The inventors treated the mice with LPS for the last two days. For decellularization of lung, the inventors perfused the lung with decellularization buffer (0.5% SDS/PBS) for 1 h and cryosectioned it and analyzed by H&E staining and immunohistochemistry 25,26. The inventors confirmed that the collagen immunofluorescence staining they observed is specific and not due to autofluorescence using a secondary only control (rabbit IgG secondary used for all anti-collagen antibodies) (data not shown). For analysis of collagen structure, the inventors used picrosirius red staining [30] and observed the structure using birefringence microscope (Abrio imaging system, CRI, MA)[30].

For transmission electron microscopy (TEM), small pieces (1-2 mm cubes) of lung tissue were fixed with 2.5% Glutaraldehyde and 2% Paraformaldehyde in 0.1 M sodium cacodylate buffer (pH 7.4) for at least 2 h at RT, washed in 0.1M cacodylate buffer and postfixed with 1% Osmiumtetroxide (OsO4)/1.5% Potassiumferrocyanide (KFeCN6) for 1 h, washed in water and incubated in 1% aqueous uranyl acetate for 1 h followed by washes in water and subsequent dehydration in grades of alcohol. The samples were then put in propyleneoxide for 1 hr and infiltrated ON in a 1:1 mixture of propyleneoxide and TAAB Epon (Marivac Canada Inc. St. Laurent, Canada). The samples were then embedded in TAAB Epon and polymerized at 60 C for 48 hrs. Ultrathin sections (about 60 nm) were cut on a Reichert Ultracut-S microtome, picked up on to copper grids stained with lead citrate and examined in a JEOL 1400 TEM microscope or a TecnaiG$^2$ Spirit BioTWIN.

BAL was performed by instilling 0.9% NaCl in two separate 0.5 ml aliquots. The fluid was recovered by gentle suction and placed on ice for immediate processing. An aliquot of the BAL fluid was processed immediately for differential cell counts performed on cytospin preparations stained with modified Wright-Giemsa stain (Diff-Quik; American Scientific Products, McGaw Park, Ill.).

Measurement of Lung Stiffness

The inventors trimmed and made cylindrical lung tissue sections using a sharp knife that included peripheral and central portions of the left lobe. The stiffness of mouse lung tissues was evaluated by determining Young's Modulus (E) under tensile loading [31,32] (Mach-1; Biomomentum, Canada). Tissues were attached to the base and probe using polyacrylamide glue and stretched until complete breakage of the tissue. The Young's Modulus was derived from the slope of a standard stress-strain curve using data within the first 10% of the maximum strain.

Statistical Analysis

All statistical data was analyzed using GraphPad Prism V5.0. Error bars (SEM) and p values were determined from the results at least three independent in vitro experiments and at least two independent in vivo experiments. The unpaired T test was used for analysis of statistical significance.

Results

ECM Mechanics Control Endothelial Cell-cell Junction Formation

Various diseases, such as cancer and fibrosis, that are accompanied by abnormal vascular permeability also exhibit altered tissue mechanics (e.g., increased stiffness)[4,13,18-20]. The inventors therefore explored whether changes in mechanical interactions between cells and ECM might regulate vascular permeability by culturing lung human microvascular endothelial (L-HMVE) cells on fibronectin-coated polyacrylamide gels with different stiffness (Young's moduli of 150 to 35,000 Pa)[15]. When cells were cultured on substrates with an intermediate stiffness (4,000 Pa), they flattened and exhibited well-developed cell-cell adhesions, whereas when the same cells were grown on more flexible substrates (150 Pa), they appeared round, VE-cadherin-containing cell-cell junctions became disrupted, and this was associated with increased VE-cadherin staining in the cytoplasm (FIG. 1A). Interestingly, cell-cell adherens junctions also were disrupted in cells cultured on abnormally rigid gels (35,000 Pa) (FIG. 1A), suggesting that a normal level of intermediate ECM stiffness is necessary to maintain optimal cell-cell junctional integrity. This effect appeared to be linked to ECM mechanics per se in that a similar trend was also observed in the L-HMVE cells cultured on different stiffness polyacrylamide gels coated with type I or type IV collagen (FIGS. 6A-6B). In addition, when the inventors stained cells with the tight junction protein, ZO1, they detected similar mechanical control of tight junction integrity by varying ECM elasticity (data not shown). Thus, ECM stiffness per se appears to be a critical determinant of pulmonary endothelial barrier function in vitro. Moreover, when endothelial cell-cell junctional integrity was measured by quantifying transendothelial electrical resistance (TEER), cells grown on the gels with intermediate stiffness (4,000 Pa) consistently displayed a highest TEER, indicating that an appropriate (intermediate) ECM stiffness is also necessary to maintain normal integrity of cell-cell junctions and associated vascular permeability barrier function in vitro (FIG. 1B).

Mechanical Control of Pulmonary Vascular Leakage In Vivo

Figures 2A, 2B, 2C, 2D:
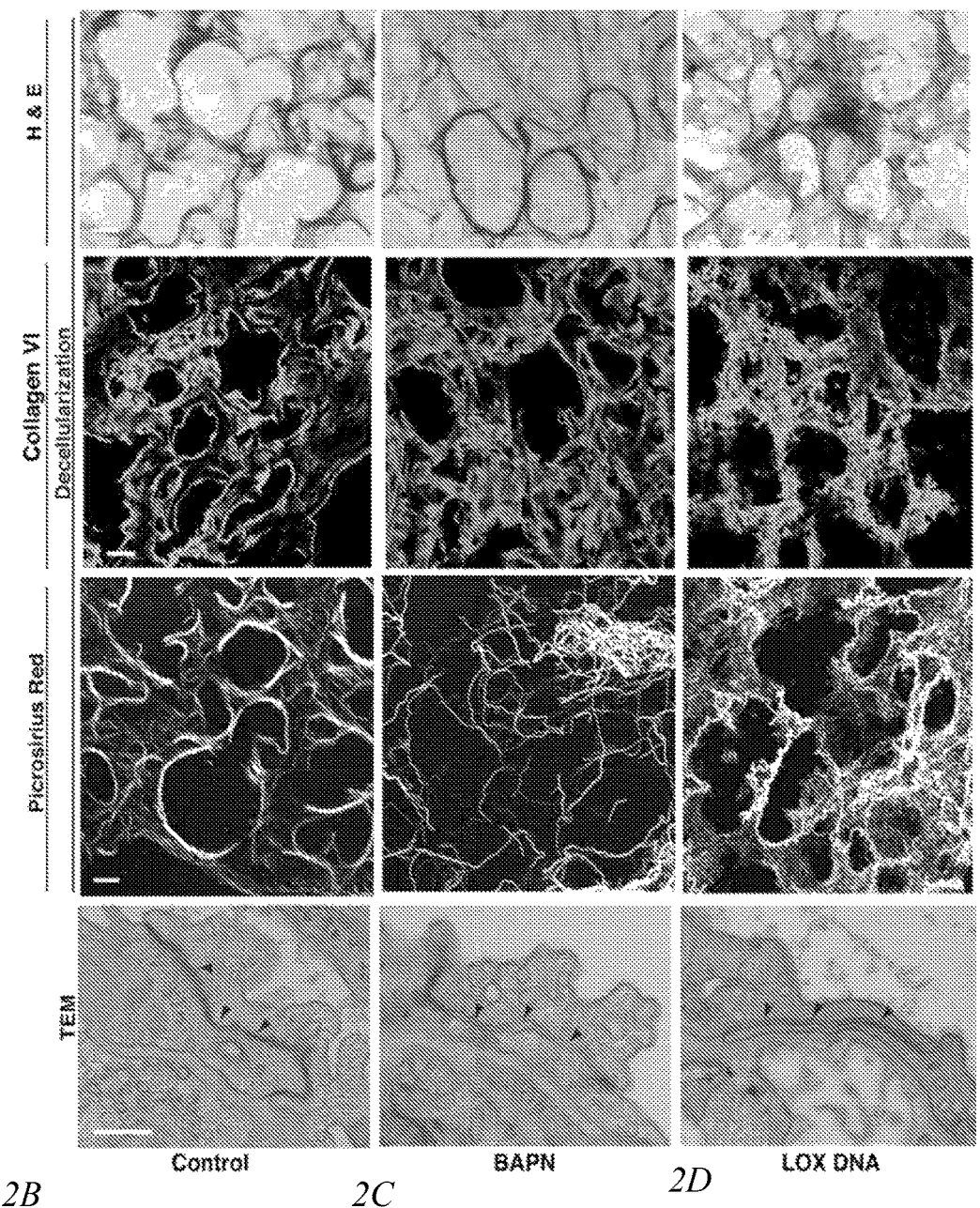
FIGS. 2A-2D demonstrate that that LOX regulates ECM structure and cell-cell junctional integrity in the lung in vivo.

To determine whether changes of ECM stiffness regulate pulmonary vascular permeability in vivo, the inventors inhibited collagen and elastin cross-linking in mice by treating them with the lysyl oxidase (LOX) activity inhibitor, beta-aminopropionitrile (BAPN) [21,22], and in separate mice, the inventors increased ECM cross-linking (and hence, rigidity) by injecting DNA encoding the LOX enzyme[3,23,24]. Treatment of mice with BAPN (which has been previously shown to disrupt collagen fiber structure in mammary tumors[13]) for 2 weeks resulted in a 25% decrease in LOX activity measured in blood samples (FIG. 2B). To directly examine whether LOX inhibition altered ECM structure, whole lungs were decellularized by perfusing mice with detergent-containing buffer (FIG. 7A). The detergent-extracted lungs extracted all of the cellular contents from the lung as detected by removal of DAPI staining (data not shown), but retained normal microarchitecture [25,26], including ECMs delineating large vessels surrounded by alveoli, alveolar septae, the characteristic spongy matrix of the lung (FIG. 2A, top) and fine ECM fibrils containing collagen I, III, IV, VI, major collagens in the lung, when analyzed by immunofluorescence microscopy (FIG. 2A and data not shown). In contrast, BAPN-treated lungs lost the fine network of collagen I, III, IV, VI-containing fibrils, and the normally well-defined borders of alveolar structures were disrupted (FIG. 2A and data not shown). However, BAPN treatment did not significantly alter mRNA expression of these collagens, and the proportion of each collagen type was similar to that exhibited by control lungs (p>0.05). The inventors confirmed these results by quantitating 4-hydroxyproline levels as a measure of the amount of collagen present in the tissue [27]. BAPN treatment did not significantly alter lung hydroxyproline levels, and there was no change in the hydroxyproline levels in serum (p>0.05), which are commonly elevated with increased collagen turnover [28]. These results indicate that the short-term (2 week) BAPN treatment the inventors utilized did not significantly alter the production or degradation of collagen in the lung.

To more carefully analyze changes in collagen structure, the inventors performed picrosirius red staining which detects fibrillar collagen (types I-V)[29] within decellularized lung sections, and examined collagen fiber microarchitecture using birefringence microscopy [29,30]. In control lungs, collagen fibers aligned with the alveolar septae, whereas they appeared to be more randomly distributed in BAPN-treated lungs (FIG. 2A). Thus, continuous ECM cross-linking appears to be required to maintain normal alveolar architecture in whole lung.

The junctional integrity of the pulmonary endothelium was also analyzed in control and BAPN-treated mice using transmission electron microscopy (TEM). Junctions between pulmonary endothelial cells were tight and characterized by closely apposed membranes in randomly sampled regions of lung from untreated mice. In contrast, cell-cell junctions appeared to be disrupted with increased space appearing between adjacent cell membranes in lungs from BAPN-treated mice (FIG. 2A).

Figures 3A, 3B, 3C:
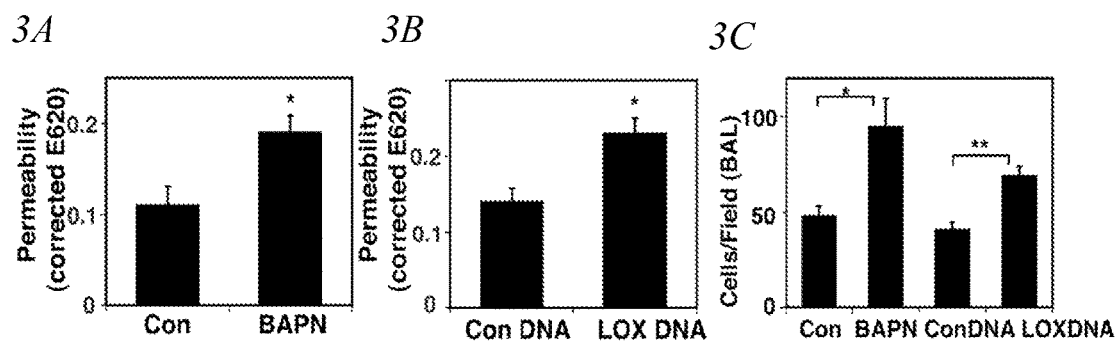
FIGS. 3A-3C demonstrate that LOX regulates lung vascular permeability in vivo.
Figures 8A, 8B:
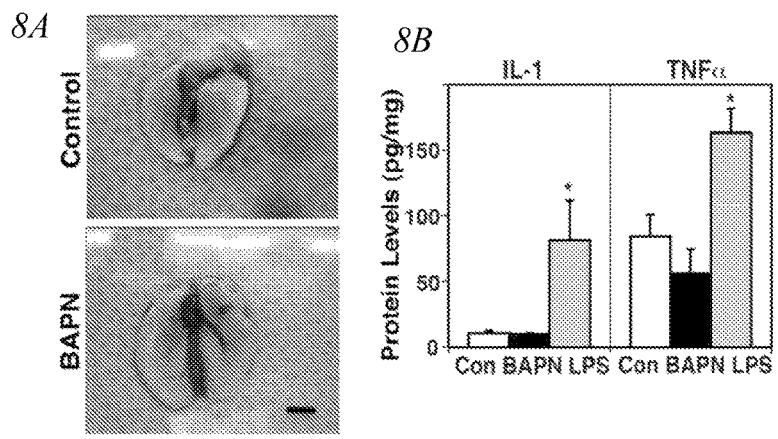
FIGS. 8A-8B demonstrate the effects of LOX on inflammation in vivo.

When the inventors measured lung mechanics using a tensile loading assay [31,32], the stiffness (Young's modulus) of BAPN-treated lung was found to decrease by 40% compared with controls (FIG. 2C), as expected from treatment with this ECM cross-linking inhibitor. Importantly, BAPN treatment also increased lung vascular permeability, as detected by leakage of fluorescently labeled low molecular weight (MW) dextran (data not shown) or Evan's Blue dye; leakage was more than 60% higher than in control non-treated lungs (FIG. 3A and FIG. 8A). In addition, BAPN treatment increased inflammatory cells in the bronchoalveolar lavage (BAL) fluid by approximately 2-fold, and this was mainly attributable to an increase in neutrophils and monocytes (FIG. 3C). However, BAPN treatment did not significantly increase the levels of the key inflammatory mediators, IL-1 or TNFα in the lung when analyzed by ELISA (FIG. 8B). These findings are consistent with BAPN increasing lung vascular permeability by changing ECM structure and mechanics, rather than by inducing secondary inflammatory effects. The finding that BAPN treatment also did not produce detectable changes in lung cell proliferation or apoptosis in vivo (not shown), further suggests that the observed effects of BAPN on vascular permeability are due to direct disruption of junction integrity, and not to cell death.

Stimulation of ECM cross-linking through over-expression of LOX DNA by retro-orbital injection, which increased LOX mRNA and protein expression in the lung (FIG. 2D, FIG. 7B), but not in other organs, such as the kidney (not shown), increased lung stiffness (FIG. 2C) and pulmonary vascular permeability (FIG. 3B) by 1.5-fold compared to lungs treated with control DNA. LOX DNA over-expression also increased the total number of inflammatory cells in the BAL fluid by approximately 1.5-fold (FIG. 3C). While retro-orbital injection of LOX DNA increased LOX expression in the lung (FIG. 2D & FIG. 7B), it did not change protein levels of the other major LOXL isoform, LOXL1 (FIG. 7B); LOXL2 levels were not detectable in healthy mouse lungs, as reported previously[33]. Thus, the effects of LOX DNA on lung vascular permeability appear to be specifically due to the change in expression of the LOX isoform. In addition, LOX DNA over-expression resulted in disruption of fine collagen fibril structures (FIG. 2A) when compared to lungs treated with control DNA where the ECM structures appeared well-organized (data not shown), but it did not produce any significant effect ($p>0.05$) on mRNA expression of collagen types I, III, IV, or VI. Importantly, LOX DNA over-expression also increased opening of junctions between pulmonary endothelial cells (FIG. 2A).

Figures 9A, 9B, 9C, 9D:
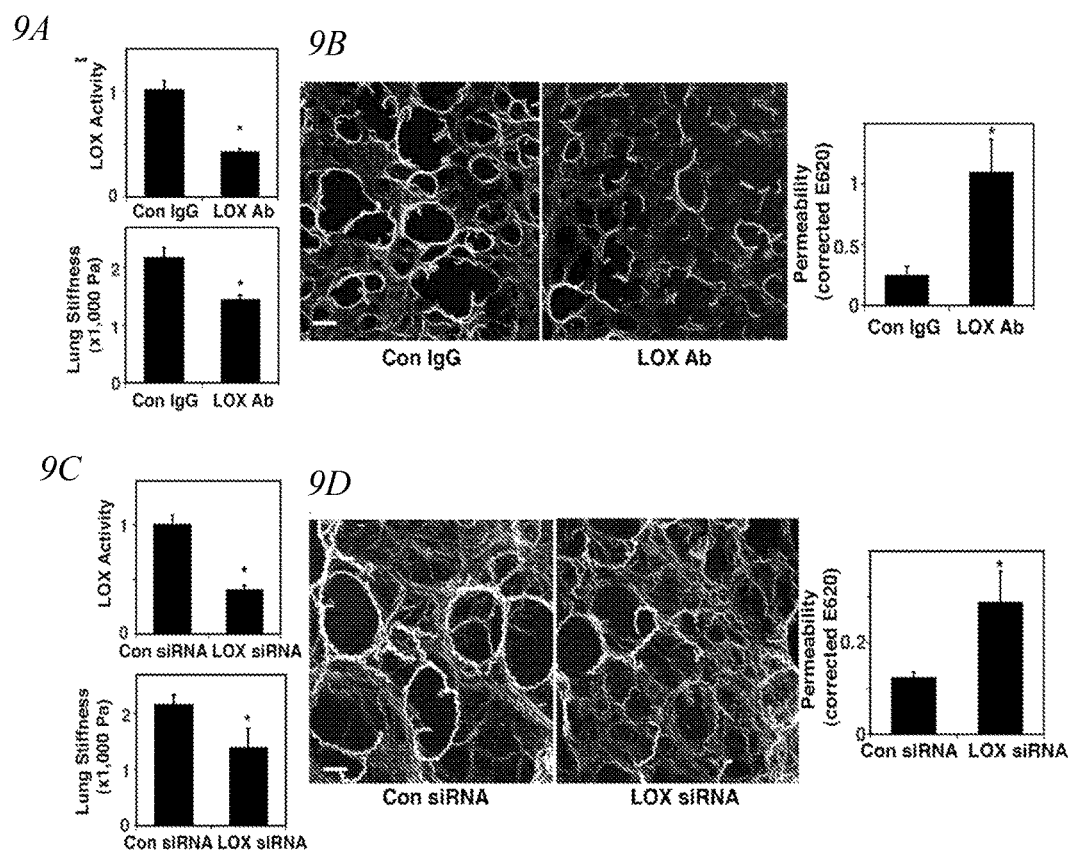
FIGS. 9A-9D demonstrate that LOX regulates lung vascular permeability in vivo.

One potential caveat in these studies is that BAPN can block other amine oxidases and it can suppress the activity of LOXL1-4 isoforms in addition to inhibiting LOX[33-35]. To more directly modify this pathway, the inventors treated mice with a LOX-specific antibody (Ab)[13,36], which has been previously shown to inhibit LOX activity and disrupt collagen organization in vitro and in vivo[13,36,37]. Treatment with this LOX inhibitory Ab resulted in a 60% decrease in LOX activity measured in blood samples and it decreased lung stiffness by 30% compared to control IgG treated lungs when measured using the tensile loading assay (FIG. 9A). The inventors also treated mice with LOX-specific siRNA for 1 week[13], which resulted in a 60% decrease in LOX activity measured in blood samples (FIG. 9C) and specifically decreased LOX expression in the lung (FIG. 7D), but not in the kidney (not shown). Treatment with LOX-specific siRNA for 1 week[13] also decreased lung stiffness by 30% compared to control siRNA treated lungs (FIG. 9C). In addition, LOX Ab or LOX siRNA treatment disrupted normal collagen fiber alignment surrounding alveolar septae (FIGS. 9B & 9D), and increased vascular permeability by 4-and 2.5-fold, respectively (FIG. 9B & 9D). Thus, the activity of the LOX isoform itself appears to control normal alveolar architecture and vascular permeability in whole mouse lung.

Figures 4A, 4B, 4C, 4D, 4E:
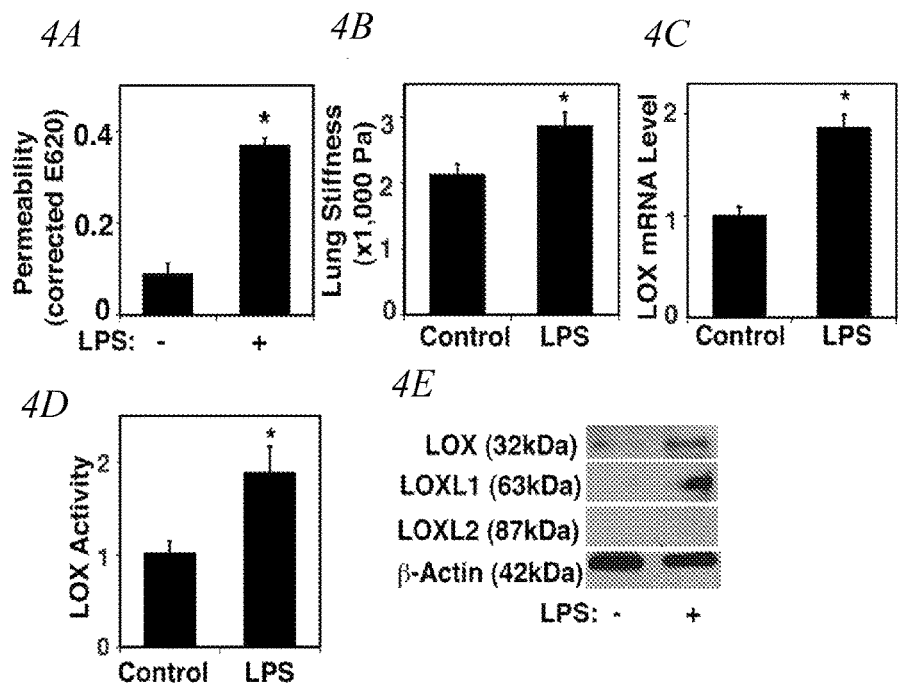
FIGS. 4A-4E demonstrate lung vascular permeability in endotoxin-induced lung injury in vivo.
Figure 5A:
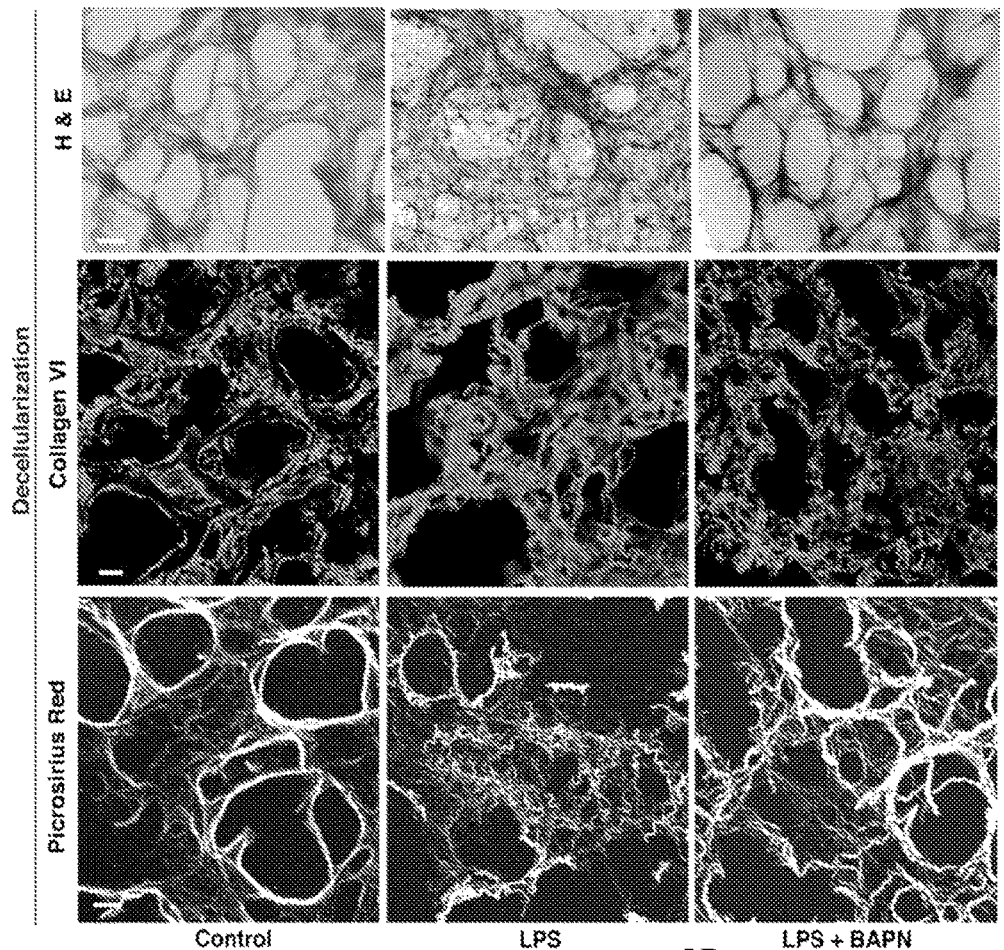
FIGS. 5A-5D demonstrate that ECM structure mediates lung vascular permeability in endotoxin-induced lung injury in vivo.
Figure 5B:
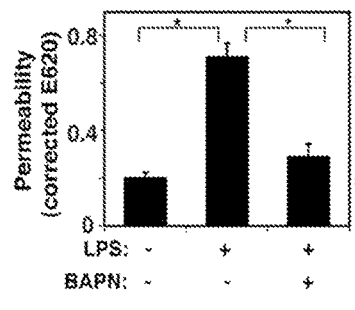
Figure 5C:
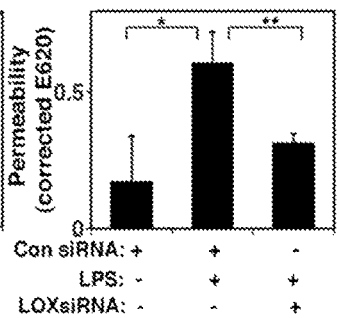
Figure 5D:
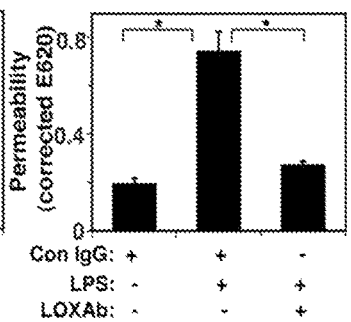
Figure 10:
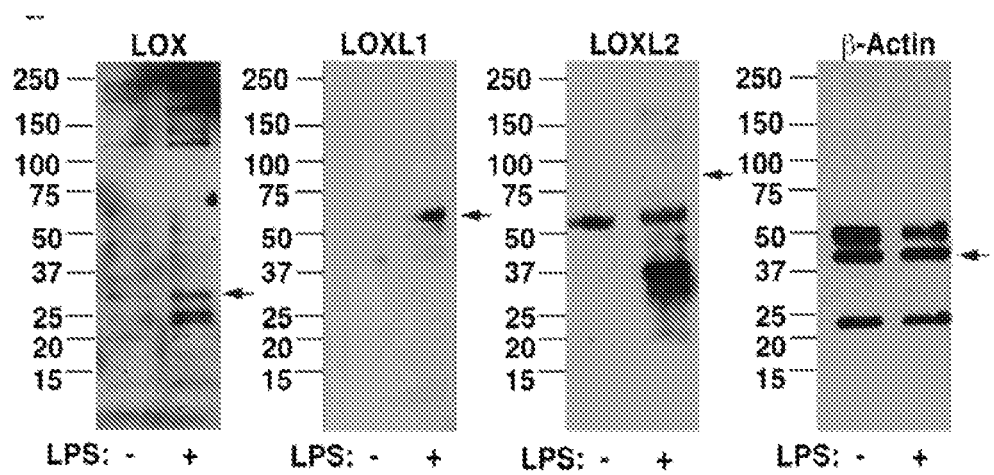
FIG. 10 shows that LOX mediates lung vascular permeability in endotoxin-induced lung injury in vivo Immunoblots showing LOX, LOXL1, LOXL2 and β-actin protein levels in mouse lungs treated with LPS. Arrows indicate the bands of each protein.

To determine the potential clinical relevance of this pathway, the inventors exposed whole lung of living adult mice to the endotoxin, lipopolysaccharide (LPS), which contributes to development of pulmonary edema and ARDS in humans with sepsis[3]. Because sepsis is one of the leading causes of ARDS, systemic LPS treatment is a widely accepted physiological animal model for sepsis-induced ARDS[3,38]. LPS treatment for 2 days increased lung vascular permeability by 4-fold compared to control untreated mice (FIG. 4A). Interestingly, when the inventors measured the material properties of mouse lungs under tensile loading, LPS-treated lungs also were 35% stiffer than control non-treated lungs (FIG. 4B), and they consistently exhibited LOX mRNA levels and activities that were 2-fold and 1.8-fold higher than those observed in control lungs, respectively (FIGS. 4C-4D). LPS treatment also increased LOX and LOXL1 protein levels, but had no effect on LOXL2 protein levels (FIG. 4E, FIG. 10). In addition, the inventors found that collagen VI-positive ECM fibers were disrupted by LPS when analyzed in decellularized lungs (FIG. 5A & data not shown), a pattern that was similar to that seen in lungs treated with LOX DNA (FIG. 2A & data not shown), and BAPN treatment prevented this disruption (FIG. 5A). Importantly, BAPN also prevented the increase of vascular permeability induced by LPS (FIG. 5B & FIG. 10). In addition, the inventors confirmed that this effect is caused by changes in activity of the LOX isoform by showing that the increase of vascular permeability induced by LPS was restored by treatment with either LOX-specific siRNA or with LOX inhibitory Ab (FIGS. 5C-5D). These findings suggest that endotoxin-induced increases in vascular permeability during development of pulmonary edema are mediated by changes in ECM structure and mechanics.

REFERENCES

1 Bryan, B. A. & D'Amore, P. A. What tangled webs they weave: Rho-GTPase control of angiogenesis. *Cell Mol Life Sci* 64, 2053-2065 (2007).

2 Orr, A. W. et al. Matrix-specific p21-activated kinase activation regulates vascular permeability in atherogenesis. *J Cell Biol* 176, 719-727 (2007).

3 Mammoto, T. et al. Angiopoietin-1 requires p190RhoGAP to protect against vascular leakage in vivo. *J Biol Chem* 282, 23910-23918 (2007).

4 Satchi-Fainaro, R. et al. Inhibition of vessel permeability by TNP-470 and its polymer conjugate, caplostatin. *Cancer Cell* 7, 251-261 (2005).

5 Matthay, M. A. & Zimmerman, G. A. Acute lung injury and the acute respiratory distress syndrome: four decades of inquiry into pathogenesis and rational management. *Am J Respir Cell Mol Biol* 33, 319-327 (2005).

6 Spragg, R. G. et al. Beyond mortality: future clinical research in acute lung injury. *Am J Respir Crit Care Med* 181, 1121-1127 (2010).

7 Nagy, J. A., Benjamin, L., Zeng, H., Dvorak, A. M. & Dvorak, H. F. Vascular permeability, vascular hyperpermeability and angiogenesis. *Angiogenesis* (2008).

8 Petrache, I., Birukova, A., Ramirez, S. I., Garcia, J. G. & Verin, A. D. The role of the microtubules in tumor necrosis factor-alpha-induced endothelial cell permeability. *Am J Respir Cell Mol Biol* 28, 574-581 (2003).

9 Birukova, A. A., Adyshev, D., Gorshkov, B., Birukov, K. G. & Verin, A. D. ALK5 and Smad4 are involved in TGF-beta1-induced pulmonary endothelial permeability. *FEBS Lett* 579, 4031-4037 (2005).

10 Fainaru, O. et al. Doxycycline induces membrane expression of VE-cadherin on endothelial cells and prevents vascular hyperpermeability. *Faseb J* 22, 3728-3735 (2008).

11 Koh, H. et al. Vascular endothelial growth factor in epithelial lining fluid of patients with acute respiratory distress syndrome. *Respirology* 13, 281-284 (2008).

12 Mura, M., dos Santos, C. C., Stewart, D. & Liu, M. Vascular endothelial growth factor and related molecules in acute lung injury. *J Appl Physiol* 97, 1605-1617 (2004).

13 Levental, K. R. et al. Matrix crosslinking forces tumor progression by enhancing integrin signaling. *Cell* 139, 891-906 (2009).

14 Paszek, M. J. et al. Tensional homeostasis and the malignant phenotype. *Cancer Cell* 8, 241-254 (2005).

15 Mammoto, A. et al. A mechanosensitive transcriptional mechanism that controls angiogenesis. *Nature* 457, 1103-1108 (2009).

16 Engler, A. J., Sen, S., Sweeney, H. L. & Discher, D. E. Matrix elasticity directs stem cell lineage specification. *Cell* 126, 677-689 (2006).

17 Ghosh, K. et al. Tumor-derived endothelial cells exhibit aberrant Rho-mediated mechanosensing and abnormal angiogenesis in vitro. *Proc Natl Acad Sci USA* 105, 11305-11310 (2008).

18 Liu, F. et al. Feedback amplification of fibrosis through matrix stiffening and COX-2 suppression. *J Cell Biol* 190, 693-706 (2010).

19 Li, L. F., Liao, S. K., Huang, C. C., Hung, M. J. & Quinn, D. A. Serine/threonine kinase-protein kinase B and extracellular signal-regulated kinase regulate ventilator-induced pulmonary fibrosis after bleomycin-induced acute lung injury: a prospective, controlled animal experiment. *Crit Care* 12, R103 (2008).

20 Huynh, J. et al. Age-related intimal stiffening enhances endothelial permeability and leukocyte transmigration. *Sci Transl Med* 3, 112-122 (2011).

21 Lucero, H. A. & Kagan, H. M. Lysyl oxidase: an oxidative enzyme and effector of cell function. *Cell Mol Life Sci* 63, 2304-2316 (2006).

22 Alcudia, J. F. et al. Lysyl oxidase and endothelial dysfunction: mechanisms of lysyl oxidase down-regulation by pro-inflammatory cytokines. *Front Biosci* 13, 2721-2727 (2008).

23 Mammoto, T. et al. Mechanochemical Control of Mesenchymal Condensation and Embryonic Tooth Organ Formation. *Dev Cell* 21, 758-769 (2011).

24 Yardeni, T., Eckhaus, M., Morris, H. D., Huizing, M. & Hoogstraten-Miller, S. Retro-orbital injections in mice. *Lab Anim (NY)* 40, 155-160 (2011).

25 Gilbert, T. W., Sellaro, T. L. & Badylak, S. F. Decellularization of tissues and organs. *Biomaterials* 27, 3675-3683 (2006).

26 Price, A. P., England, K. A., Matson, A. M., Blazar, B. R. & Panoskaltsis-Mortari, A. Development of a Decellularized Lung Bioreactor System for Bioengineering the Lung: The Matrix Reloaded. *Tissue Eng Part A* 16, 2581-2591 (2010).

27 Atabai, K. et al. Mfge8 diminishes the severity of tissue fibrosis in mice by binding and targeting collagen for uptake by macrophages. *J Clin Invest* 119, 3713-3722 (2009).

28 Miller, L. F., Judge, M. D. & Schanbacher, B. D. Intramuscular collagen and serum hydroxyproline as related to implanted testosterone, dihydrotestosterone and estradiol-17 beta in growing wethers. *J Anim Sci* 68, 1044-1048 (1990).

29 Junqueira, L. C., Cossermelli, W. & Brentani, R. Differential staining of collagens type I, II and III by Sirius Red and polarization microscopy. *Arch Histol Jpn* 41, 267-274 (1978).

30 Junqueira, L. C., Bignolas, G. & Brentani, R. R. Picrosirius staining plus polarization microscopy, a specific method for collagen detection in tissue sections. *Histochem J* 11, 447-455 (1979).

31 Ito, S. et al. Mechanics, nonlinearity, and failure strength of lung tissue in a mouse model of emphysema: possible role of collagen remodeling. *J Appl Physiol* 98, 503-511 (2005).

32 Al Jamal, R., Roughley, P. J. & Ludwig, M. S. Effect of glycosaminoglycan degradation on lung tissue viscoelasticity. *Am J Physiol Lung Cell Mol Physiol* 280, L306-315 (2001).

33 Barry-Hamilton, V. et al. Allosteric inhibition of lysyl oxidase-like-2 impedes the development of a pathologic microenvironment. *Nat Med* 16, 1009-1017 (2010).

34 Rodriguez, H. M. et al. Modulation of lysyl oxidase-like 2 enzymatic activity by an allosteric antibody inhibitor. *J Biol Chem* 285, 20964-20974 (2010).

35 Trackman, P. C. & Kagan, H. M. Nonpeptidyl amine inhibitors are substrates of lysyl oxidase. *J Biol Chem* 254, 7831-7836 (1979).

36 Kanapathipillai, M. et al. Inhibition of mammary tumor growth using lysyl oxidase-targeting nanoparticles to modify extracellular matrix. *Nano Lett* 12, 3213-3217 (2012).

37 Erler, J. T. et al. Lysyl oxidase is essential for hypoxia-induced metastasis. *Nature* 440, 1222-1226 (2006).

38 Matute-Bello, G., Frevert, C. W. & Martin, T. R. Animal models of acute lung injury. *Am J Physiol Lung Cell Mol Physiol* 295, L379-399 (2008).

39 Kumarasamy, A. et al. Lysyl oxidase activity is dysregulated during impaired alveolarization of mouse and human lungs. *Am J Respir Crit Care Med* 180, 1239-1252 (2009).

40 Rodriguez, C. et al. Regulation of lysyl oxidase in vascular cells: lysyl oxidase as a new player in cardiovascular diseases. *Cardiovasc Res* 79, 7-13 (2008).

41 Maki, J. M. et al. Inactivation of the lysyl oxidase gene Lox leads to aortic aneurysms, cardiovascular dysfunction, and perinatal death in mice. *Circulation* 106, 2503-2509 (2002).

42 Stamenovic, D. & Ingber, D. E. Models of cytoskeletal mechanics of adherent cells. *Biomech Model Mechanobiol* 1, 95-108 (2002).

43 Dejana, E. Endothelial cell-cell junctions: happy together. *Nat Rev Mol Cell Biol* 5, 261-270 (2004).

44 Provenzano, P. P. & Keely, P. J. Mechanical signaling through the cytoskeleton regulates cell proliferation by coordinated focal adhesion and Rho GTPase signaling. *J Cell Sci* 124, 1195-1205 (2011).

45 Mammoto, A., Mammoto, T. & Ingber, D. E. Rho signaling and mechanical control of vascular development. *Curr Opin Hematol* 15, 228-234 (2008).

46 Mammoto, A., Huang, S. & Ingber, D. E. Filamin links cell shape and cytoskeletal structure to Rho regulation by controlling accumulation of p190RhoGAP in lipid rafts. *J Cell Sci* 120, 456-467 (2007).

47 Wojciak-Stothard, B., Potempa, S., Eichholtz, T. & Ridley, A. J. Rho and Rac but not Cdc42 regulate endothelial cell permeability. *J Cell Sci* 114, 1343-1355 (2001).

48 Taylor, M. A., Amin, J. D., Kirschmann, D. A. & Schiemann, W. P. Lysyl oxidase contributes to mechanotransduction-mediated regulation of transforming growth factor-beta signaling in breast cancer cells. *Neoplasia* 13, 406-418 (2011).

49 Onoda, M. et al. Lysyl oxidase resolves inflammation by reducing monocyte chemoattractant protein-1 in abdominal aortic aneurysm. *Atherosclerosis* 208, 366-369 (2010).
50 Chen, C. Z. & Raghunath, M. Focus on collagen: in vitro systems to study fibrogenesis and antifibrosis state of the art. *Fibrogenesis Tissue Repair* 2, 7 (2009).
51 Bruel, A., Ortoft, G. & Oxlund, H Inhibition of cross-links in collagen is associated with reduced stiffness of the aorta in young rats. *Atherosclerosis* 140, 135-145 (1998).
52 Bank, R. A. & van Hinsbergh, V. W. Lysyl oxidase: new looks on LOX. *Arterioscler Thromb Vasc Biol* 22, 1365-1366 (2002).
53 Hecquet, C. M., Ahmmed, G. U. & Malik, A. B. TRPM2 channel regulates endothelial barrier function. *Adv Exp Med Biol* 661, 155-167 (2010).
54 Shieh, T. M. et al. Association of expression aberrances and genetic polymorphisms of lysyl oxidase with areca-associated oral tumorigenesis. *Clin Cancer Res* 13, 4378-4385 (2007).
55 Fogelgren, B. et al. Cellular fibronectin binds to lysyl oxidase with high affinity and is critical for its proteolytic activation. *J Biol Chem* 280, 24690-24697 (2005).
56 Wang, N. et al. Cell prestress. I. Stiffness and prestress are closely associated in adherent contractile cells. *Am J Physiol Cell Physiol* 282, C606-616 (2002).
57 Kim, H. J., Huh, D., Hamilton, G. & Ingber, D. E. Human gut-on-a-chip inhabited by microbial flora that experiences intestinal peristalsis-like motions and flow. *Lab Chip* 12, 2165-2174 (2012).
58 Bolcato-Bellemin, A.-L., Bonnet, M.-E. & Erbache, P. In vivo Delivery of DNA or siRNA Formulated into Nanoparticles with Linear PEI. *Molecular Therapy* 13, S69, doi: 10.1016/j.ymthe.2006.08.203 (2006).
59 Bonnet, M. E., Erbacher, P. & Bolcato-Bellemin, A. L. Systemic delivery of DNA or siRNA mediated by linear polyethylenimine (L-PEI) does not induce an inflammatory response. *Pharm Res* 25, 2972-2982 (2008).

Example 2

As described herein, collagen structure and remodeling control vascular permeability and the LOX inhibitor BAPN inhibits LPS-induced pulmonary edema in mice. However, due to its non-specific chemical effects and toxicity, BAPN has not been FDA-approved yet. LOX is a copper-dependent enzyme and copper is essential for the functional activity of this enzyme including extracellular processing of collagens and elastin. D-penicillamine is a FDA-approved agent used to treat intracerebral copper overload in Wilson's disease. Therefore, it was explored whether D-penicillamine suppresses endotoxin-induced lung vascular permeability in mice. When mice were treated with D-penicillamine (8 mg/mouse/day, IP) for two days, vascular permeability induced by LPS treatment evaluated by Evans blue dye leakage was suppressed by 40%. It is contemplated herein that D-penicillamine restores the ECM structure in the lung treated with LPS.

What is claimed is:

1. A method of decreasing vascular permeability in a tissue or organ of a subject in need of treatment for a pulmonary disease selected from acute respiratory distress syndrome (ARDS), pulmonary edema, endotoxin-induced lung injury, pulmonary embolism, pleural effusion, or sepsis, the method comprising:
   administering an agent that decreases the stiffness of the extracellular matrix (ECM) to a subject in need thereof wherein the agent is a lysyl oxidase (LOX) inhibitor selected from the group consisting of: a lysyl oxidase (LOX) siRNA, a peptide having the sequence EDTSCDYGYHRRFA (SEQ ID NO: 1), or a purified antibody that binds specifically to the sequence EDTSCDYGYHRRFA (SEQ ID NO: 1).

2. The method of claim 1, further comprising measuring the ECM in the subject before treatment.

3. The method of claim 1, wherein the agent is administered via aerosol delivery into the subject's lung.

* * * * *